US012000783B2

United States Patent
Wada et al.

(10) Patent No.: US 12,000,783 B2
(45) Date of Patent: Jun. 4, 2024

(54) DEVICE FOR DETECTING SUBSTANCE BEING MEASURED

(71) Applicant: CITIZEN WATCH CO., LTD., Tokyo (JP)

(72) Inventors: Kana Wada, Saitama (JP); Takaaki Nozaki, Saitama (JP)

(73) Assignee: CITIZEN WATCH CO., LTD., Tokyo (JP)

( * ) Notice: Subject to any disclaimer, the term of this patent is extended or adjusted under 35 U.S.C. 154(b) by 331 days.

(21) Appl. No.: 17/626,124

(22) PCT Filed: Jul. 10, 2020

(86) PCT No.: PCT/JP2020/027148
§ 371 (c)(1),
(2) Date: Jan. 11, 2022

(87) PCT Pub. No.: WO2021/006356
PCT Pub. Date: Jan. 14, 2021

(65) Prior Publication Data
US 2022/0276165 A1 Sep. 1, 2022

(30) Foreign Application Priority Data

Jul. 11, 2019 (JP) .................................. 2019-129311
Jan. 17, 2020 (JP) .................................. 2020-006249

(51) Int. Cl.
*G01N 21/00* (2006.01)
*B03C 1/01* (2006.01)
(Continued)

(52) U.S. Cl.
CPC .............. *G01N 21/64* (2013.01); *B03C 1/01* (2013.01); *B03C 1/02* (2013.01); *G01R 33/0017* (2013.01)

(58) Field of Classification Search
CPC ..... G01N 21/64; G01N 33/483; G01N 33/543
See application file for complete search history.

(56) References Cited

U.S. PATENT DOCUMENTS 8,193,003 B2 * 6/2012 Tsukamoto ...... G01N 33/54333
435/7.1
9,506,919 B2 * 11/2016 Gaster ................. G01N 27/745
(Continued)

FOREIGN PATENT DOCUMENTS

JP       H06-207938 A    7/1994
JP       2010-133777 A   6/2010
(Continued)

OTHER PUBLICATIONS

WIPO, International Search Report for International Application No. PCT/JP2020/027148, dated Oct. 6, 2020.
(Continued)

*Primary Examiner* — Dani Fox

(57) ABSTRACT

A detection device of a substance to be measured according to an embodiment of the present disclosure is intended to conveniently detect a bio-related substance such as a bacteria or a fungus. The detection device according to an embodiment of the present disclosure includes, a container that contains solution and a composite particle combining a substance to be measured and a magnetic labeling substance, a magnetic field applying unit that applies a magnetic field to a predetermined region so as to collect the composite particles, wherein spatial light is incident to the predetermined region other than lower region of the container, an imaging unit for imaging the composite particles collected in the predetermined region where the spatial light is incident, a detection unit that detects the composite particles based on the image captured by the imaging unit.

14 Claims, 25 Drawing Sheets

(51) Int. Cl.
*B03C 1/02* (2006.01)
*G01N 21/64* (2006.01)
*G01R 33/00* (2006.01)

(56) References Cited

U.S. PATENT DOCUMENTS

| | | |
|---|---|---|
| 2019/0154580 A1 | 5/2019 | Yasuura et al. |
| 2019/0264264 A1 | 8/2019 | Connolly et al. |
| 2019/0285639 A1 | 9/2019 | Connolly et al. |

FOREIGN PATENT DOCUMENTS

| | | |
|---|---|---|
| JP | 2017-219512 A | 12/2017 |
| JP | 2020-030136 A | 2/2020 |
| WO | 2017/187744 A1 | 11/2017 |
| WO | 2018/081440 A1 | 5/2018 |

OTHER PUBLICATIONS

WIPO, Written Opinion for International Application No. PCT/JP2020/027148, dated Oct. 6, 2020.

* cited by examiner (a)                 (b)

FIG. 30
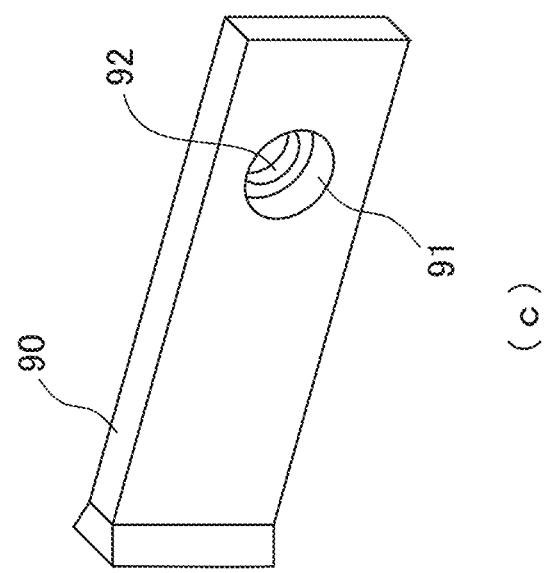
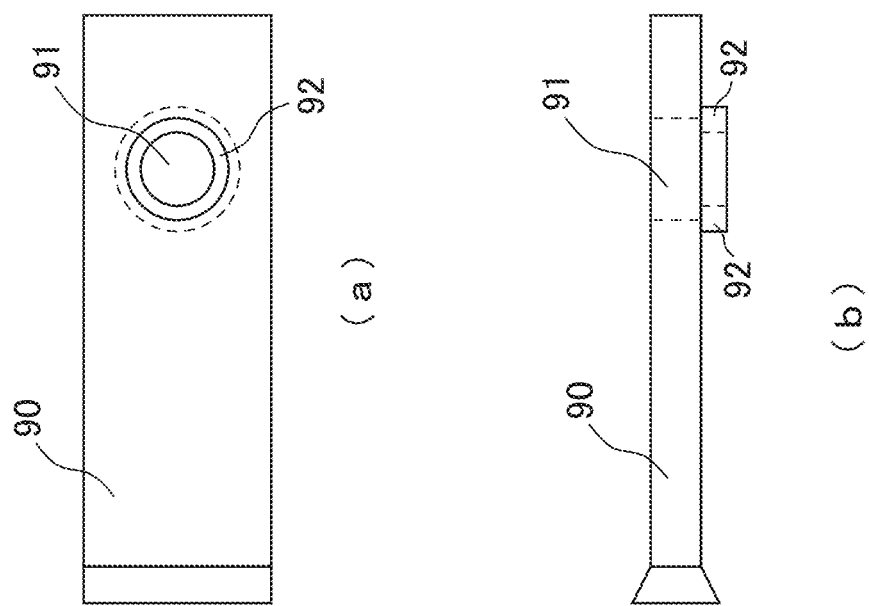

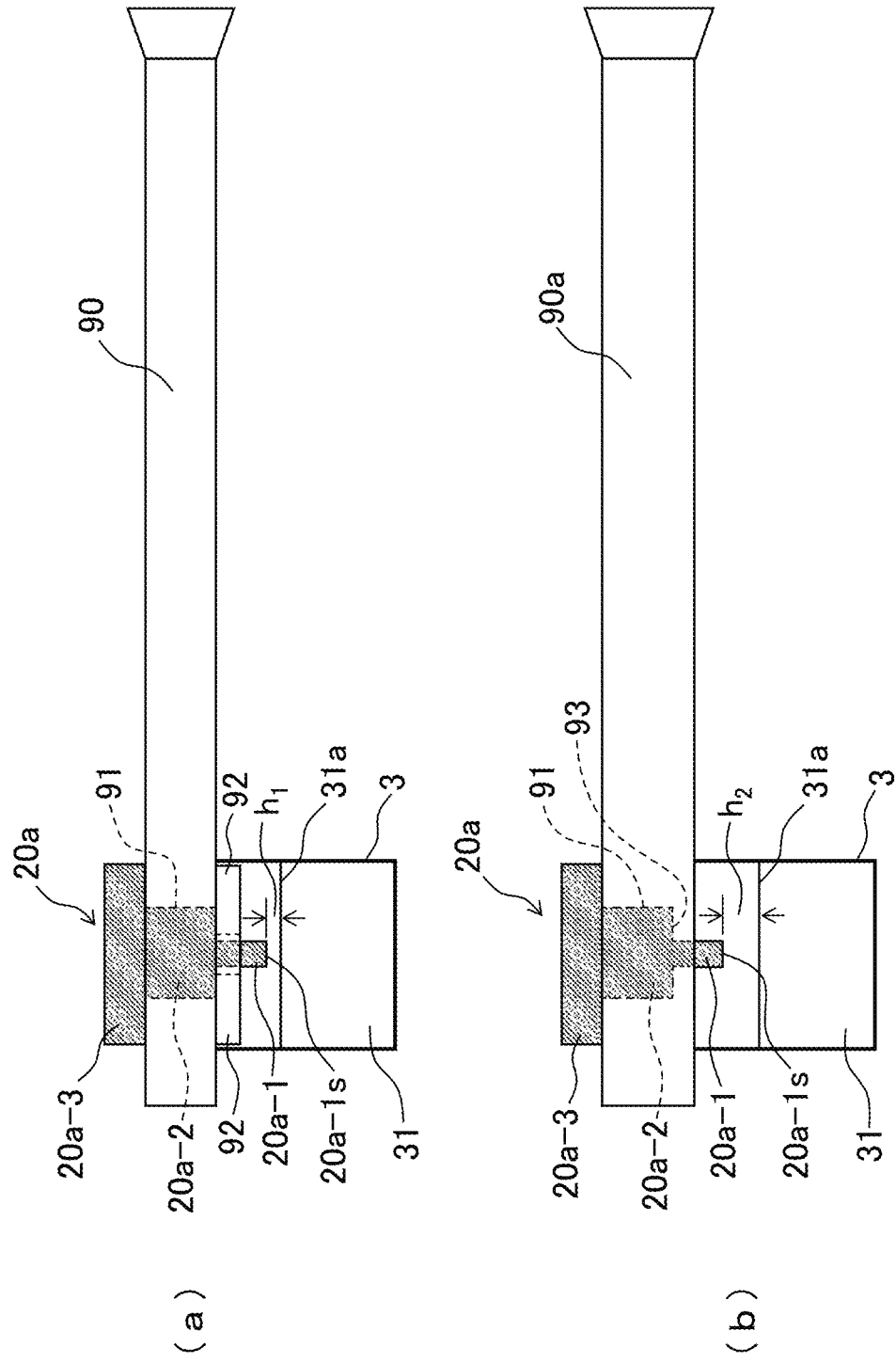

DEVICE FOR DETECTING SUBSTANCE BEING MEASURED

FIELD

The present invention relates to a detection device of a substance to be measured.

BACKGROUND

There have been increasing needs for a method for detecting a biological substance such as a virus, a bacterium, or a fungus, that exists in a solution of a biological sample. As a method of detecting a biological substance having a size of several hundreds of nanometers, such as a virus, an optical detection method using near-field light is known (e.g., Patent Literature 1). When light travels from a medium with a high refractive index to a medium with a low refractive index and the incident angle exceeds a certain critical angle, the light causes total reflection at the boundary surface and the light does not travel to the medium with a low refractive index. The near-field light is light bleeding out to the medium having a low refractive index with a very short length of about one wavelength of light. Near-field light is not diffracted because it does not propagate through space. Near-field light is used as a means for obtaining information on substances bellow the wavelength of light beyond the diffraction limit at the resolution of the microscope, which has been limited by the diffraction limit. Near-field light is also attracting attention as a method of processing minute substances.

However it may be difficult to detect bacteria, fungi, or other biological substances by the optical detection method with near-field light because they have a size of several micrometers.

CITATION LIST

Patent Literature

Patent Literature 1: International Publication No. WO 2017/187744 A1

SUMMARY

An object of a detection device of a substance to be measured according to an embodiment of the present disclosure is to conveniently detect a biological substance, such as a bacterium or a fungus.

A detection device according to the embodiment of the present disclosure includes a container that contains solution and a composite particle combining a substance to be measured and a magnetic labeling substance, a magnetic field applying unit that applies a magnetic field to a predetermined region so as to collect the composite particle, wherein spatial light is incident to the predetermined region other than lower region of the container, an imaging unit that captures an image of the composite particle collected in the predetermined region where the spatial light is incident, and a detecting unit that detects the composite particle based on the image captured by the imaging unit.

Preferably, the imaging unit is disposed at a position facing the container across the magnetic field applying unit, and the magnetic field applying unit moves to a position relative to the container where the magnetic field applying unit does not interfere capturing the image by the imaging unit when the imaging unit captures the image.

Preferably, the magnetic field applying unit includes a first plane member opposed to the upper surface of the solution, and a second plane member facing the imaging unit, and an area of the first plane member is smaller than an area of the second plane member.

Preferably, the magnetic field applying unit has a shape in which the cross-sectional area increases continuously or stepwise, as it proceeds upward from the lower end of the magnetic field applying unit.

Preferably, the magnetic field applying unit applies the magnetic field to the solution so that the composite particle is distributed in an imaging region where the imaging unit captures an image.

Preferably, the imaging region captured by the imaging unit is a part of the region occupied by the container, and the closest portion of the upper surface side of the solution in the magnetic field applying unit has a size included in the imaging region.

Preferably, the magnetic field applying unit has a plurality of laminated magnets.

Preferably, the magnetic field applying unit has an integrally molded magnet.

Preferably, the plurality of magnets have a cylindrical shape or a prismatic shape.

Preferably, the magnetic field applying unit is movable relative to the container between a position where a closest portion of an upper surface side of the solution in the magnetic field applying unit opposed to the upper surface of the solution and a position where the magnetic field applying unit does not interfere with the imaging unit capturing an image of the upper surface of the solution.

Preferably, the detection device further includes a control unit for controlling the magnetic field applying unit so that the magnetic field applying unit moves relative to the container to the position where the magnetic field applying unit does not interfere with capturing the image by the imaging unit, after the closest portion of the magnetic field applying unit moves vertically upward to a position where the influence of the magnetic field does not affect the composite particles from a position facing the upper surface of the solution.

Preferably, the magnetic field applying unit is disposed above the container, and the imaging unit is disposed below the container.

Preferably, the magnetic field applying unit has a first coil, and the imaging unit is disposed at a position facing the container across the first coil, so as to capture an image of the inside of the container through the inside of the first coil.

Preferably, the magnetic field applying unit further includes a second coil, and the second coil is disposed at a position such that a magnetic field can be applied to a position different from the position where the magnetic field is applied by the first coil.

Preferably, the magnetic field applying unit further includes a second coil, and includes a control unit configuring to stop applying the magnetic field by the first coil after first predetermined time has elapsed since start of the applying the magnetic field by the first coil, start applying the magnetic field by the second coil, and make the imaging unit capture an image after the second predetermined time has elapsed from the start of the applying the magnetic field by the second coil.

According to the detection device of the substance to be measured according to the embodiment of the present disclosure, it is possible to conveniently detect a biological substance, such as a bacterium or a fungus as compared with a case where near-field light is used.

BRIEF DESCRIPTION OF THE DRAWINGS

FIGS. 12(a) and 12(b) are images in the predetermined region in the solution imaged by the imaging unit constituting the detection device of the substance to be measured according to the fourth embodiment of the present disclosure, wherein FIG. 12(a) is an image when a magnetic field is applied only by a first coil, and FIG. 12(b) is an image when the application of the magnetic field by the first coil is stopped and a magnetic field is applied by a second coil and a third coil.

FIGS. 30(a) to 30(c) are diagrams showing an example of a holder for holding a magnet used in the detection device of the substance to be measured according to the sixth embodiment of the present disclosure, FIG. 30(a) is a plan view, FIG. 30(b) is a side view, and FIG. 30(c) is a perspective view.

FIGS. 31(a) and 31(b) are diagrams showing the positional relationship between the magnet and the solution held in the holder in the detection device of the substance to be measured according to the sixth embodiment of the present disclosure, FIG. 31(a) shows the case when using the holder shown in FIG. 30, and FIG. 31(b) shows the case when using another holder.

DESCRIPTION OF EMBODIMENTS

Hereinafter, a detection device of a substance to be measured according to embodiments of the present disclosure will be described with reference to the drawings. However, note that the technical scope of the present invention is not limited to these embodiments and includes the invention described in the claims and equivalents thereof.

First Embodiment

Figure 1:
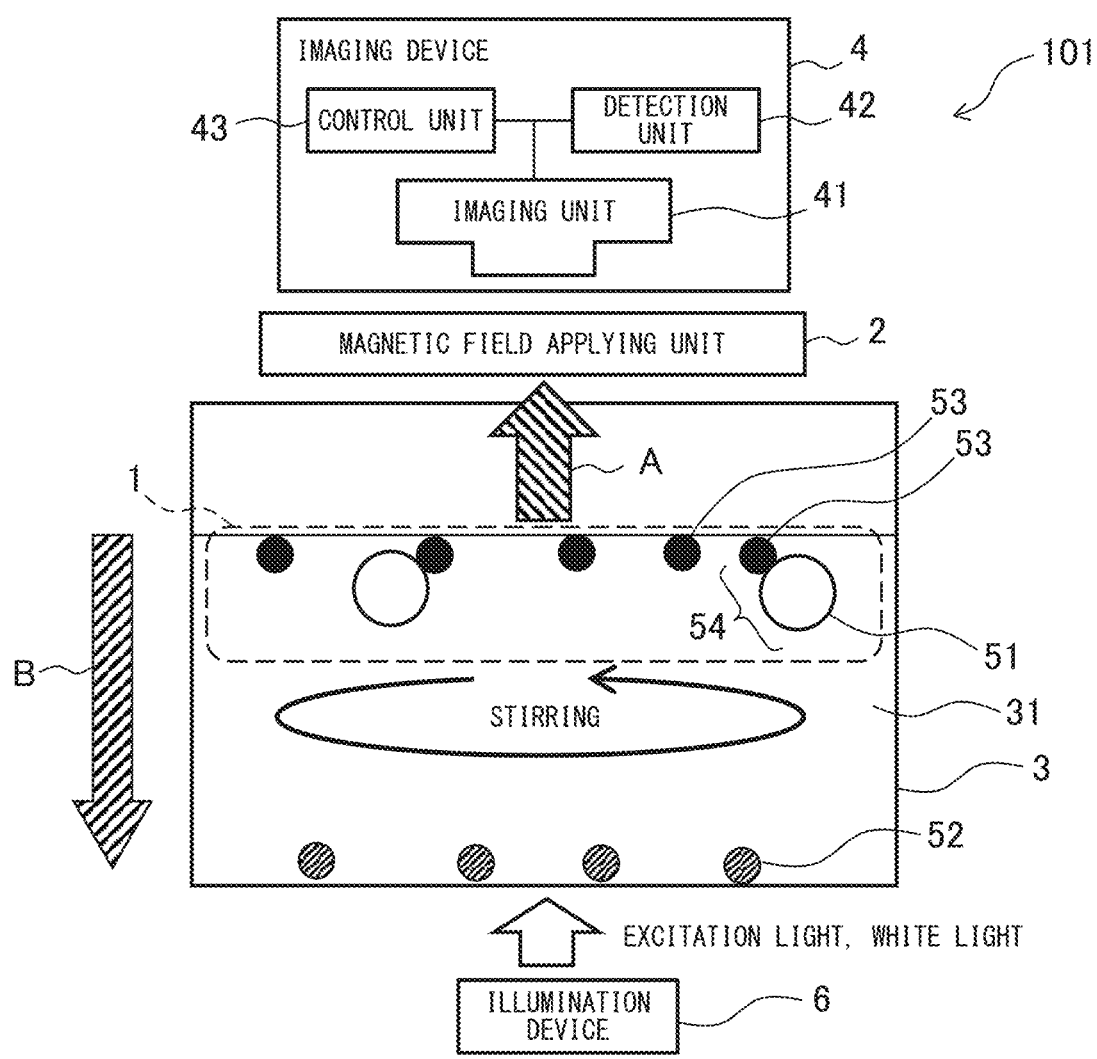
FIG. 1 is a configuration diagram of a detection device of the substance to be measured according to a first embodiment of the present disclosure.

First, a detection device of a substance to be measured according to a first embodiment of the present disclosure will be described. FIG. 1 shows a configuration diagram of a detection device 101 of the substance to be measured according to the first embodiment of the present disclosure. The detection device 101 of the substance to be measured according to the first embodiment includes a container 3, a magnetic field applying unit (magnetic field applier) 2, and an imaging device 4.

Figure 2:
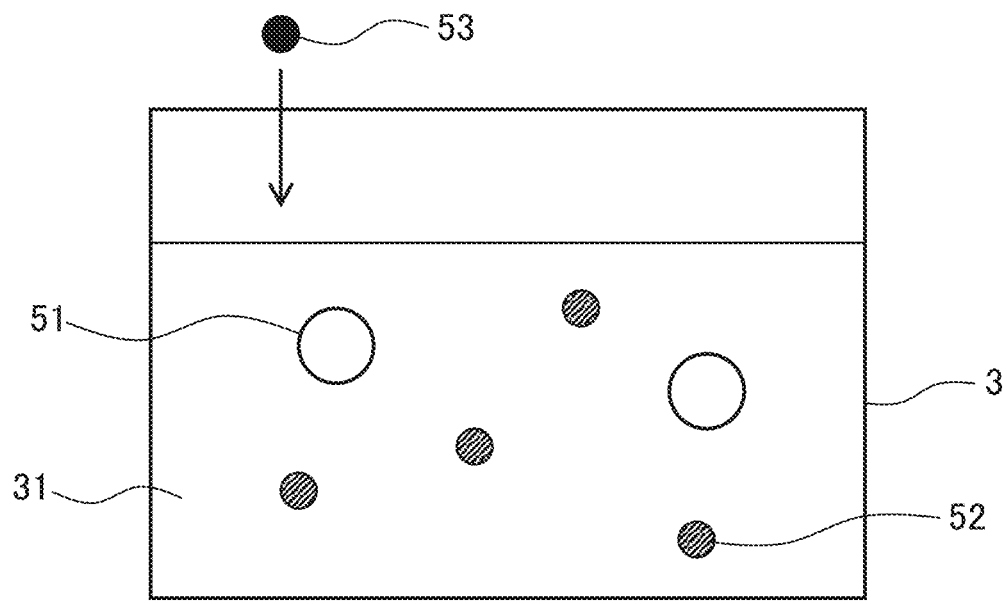
FIG. 2 is a side view of a container constituting the detection device of the substance to be measured according to the first embodiment of the present disclosure.
Figure 3:
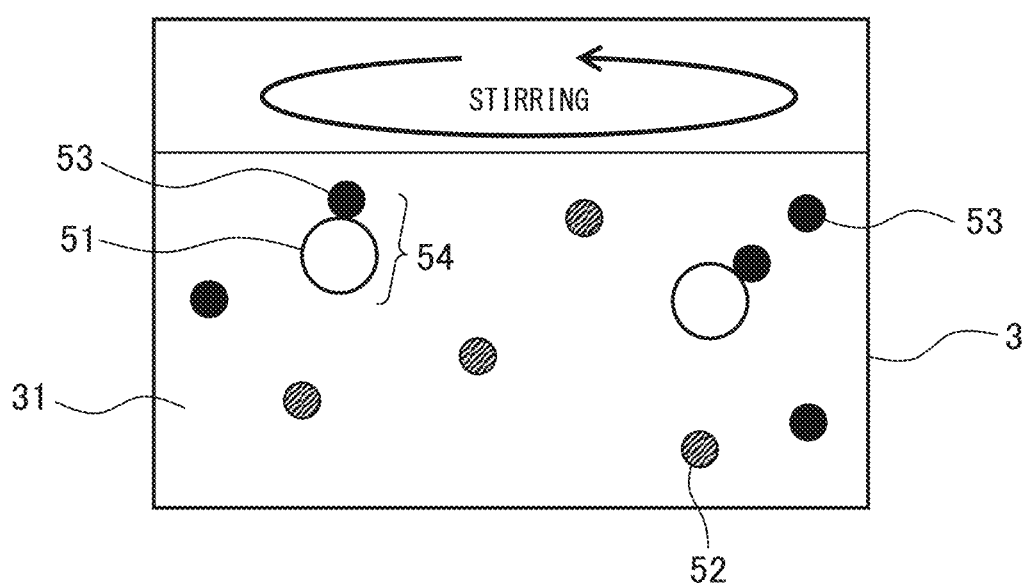
FIG. 3 is a side view of the container constituting the detection device of the substance to be measured according to the first embodiment of the present disclosure showing a state in which the substance to be measured and the magnetic labeling substance are put into a solution to facilitate a reaction by stirring.

The container 3 contains a solution 31, and a composite particle 54 in which a substance to be measured 51 and a magnetic labeling substance 53 are bonded. As the solution 31, for example, a biological sample solution is used. Examples of the biological sample solution include, for example, saliva, blood, urine, and sweat. FIG. 2 shows a side view of the container 3 constituting the detection device 101 of the substance to be measured according to the first embodiment of the present disclosure. FIG. 3 shows a side view of the container 3 constituting the detection device 101 of the substance to be measured according to the first embodiment of the present disclosure, and shows a state in which the reaction between the substance to be measured 51 and the magnetic labeling substance 53 in the solution 31 is facilitated by stirring. Preferably, the magnetic labeling substances 53 are bound to all of the substances 51 to be measured in the solution 31 to form the composite particles 54. In addition, at the time when the substance to be measured 51 and the magnetic labeling substance 53 are placed in the container 3, these substances may not be bonded. In other words, for example, a reaction in which the magnetic labeling substance 53 is bound to the substance to be measured 51 may be promoted by a flow of the solution 31 generated by stirring in the container 3 to generate the composite particles 54. Examples of the substance 51 to be measured include *Candida* bacteria, *E. coli*, and CRP (C-reactive protein)

As shown in FIG. 1, a predetermined region 1 is a region where the spatial light is incident, and is a region other than the lower region of the container 3. "Other substances" 52 precipitates in the lower region of the container 3, which is the substance that does not correspond to any of the substance to be measured 51, the magnetic labeling substance 53, and the composite particles 54. The other substances 52 include contaminants. Preferably, the predetermined region 1 is a region other than the lower region and is a reason not including the other substances 52.

Spatial light (also referred to as "propagating light") refers to general light propagating in space and does not include localized light like near-field light. Specifically, spatial light is defined as light that does not include near-field light that exhibits abrupt attenuation at a position that is generally distant from the source by a distance of several hundred nanometers to several microns, but is also meant to be free of near-field light, and means light that does not exhibit abrupt attenuation at a position that is distant from the interface between the container and the solution by a distance of several hundred nanometers to several microns. In the detection method using near-field light, a region capable of detecting the substance to be measured is limited to a range of several hundred nanometers from the surface of the solution. Since the size of bacteria and fungi is on the order of several microns, it is difficult to detect them by near-field light, and further, a detection device using near-field light has a problem that a detection substrate and an optical system become complicated. On the other hand, since the detection device of the substance to be measured according to the embodiment of the present disclosure uses spatial light, it is possible to observe the substance having a wavelength or more of the spatial light, and there is no limitation on the size of the substance to be measured 51 if it is present in the predetermined region 1. Therefore, according to the detection device of the substance to be measured according to the embodiment of the present disclosure, it is possible to detect bacteria, fungi, and the like having a size of several microns order with a simple structure. Spatial light is irradiated toward the predetermined area 1 from the illumination device 6 disposed below the container 3. However, the present invention is not limited to such an example, and the illumination device 6 may be disposed on a side surface of the container 3. Further, it is not limited to the case where the illumination device 6 is used, and natural light may be utilized as spatial light.

As a method of stirring the solution 31 in the container 3, the container 3 may be shaken by hand and stirred before being set in the detection device 101, or a stirring mechanism may be provided in the detection device 101 and stirred in the detection device 101. When the stirring mechanism is provided in the detection device 101, a method of pressing and stirring the container 3 on a disk rotating like a vortex mixer, a centrifugal stirring, an ultrasonic vibration, or the like can be utilized. Further, when the solution 31 is irradiated with the spatial light, the solution 31 is heated by light (excitation light, white light) irradiated from the illumination device 6, and convection occurs in the solution 31 by heating.

In order to collect the composite particles 54 in the predetermined region 1 other than the lower region of the container 3 where the spatial light is incident, the magnetic field applying unit 2 applies the magnetic field to the predetermined region 1. As the magnetic field applying unit 2, for example, a magnet, or an electromagnet or the like can be used.

When the magnetic field applying unit 2 is disposed on the upper portion of the container 3, unreacted magnetic labeling substance 53 and the composite particles 54 which are magnetically labeled substances to be measured are collected in the predetermined region 1 which is a detection region provided on the upper portion of the container 3. On the other hand, the other substances 52 precipitate on the bottom surface of the container 3 by gravity. The reason for collecting the composite particles 54 in the predetermined region 1 which is a region other than the lower part region of the container 3 is that the other substances 52 precipitated in the lower region of the container 3 become noise, and detection of the composite particles 54 may become difficult in some cases. According to the detection device 101 of the substance to be measured according to the first embodiment, it is possible to separate the predetermined region 1 in which the composite particles 54 are collected and the lower region in which the other substances 52 are precipitated. A posture at the time when using the detection device 101, the direction of the gravitational force is referred to as a "lower" direction of the detection device, the direction opposite to the direction of the gravity is referred to as a "upper" direction of the detection device.

Figure 4:
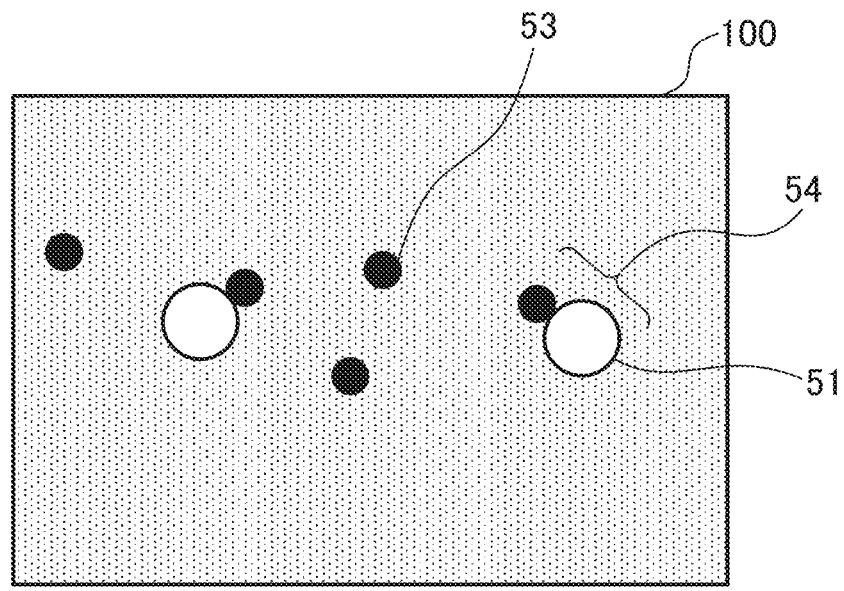
FIG. 4 is an example of an image in a predetermined region in the solution captured by the imaging unit constituting the detection device of the substance to be measured according to the first embodiment of the present disclosure.

The imaging device 4 includes an imaging unit (imager) 41, a detection unit (detector) 42, and a control unit (controller) 43. The spatial light incident on the predetermined region 1 is reflected or scattered or the like by the composite particles 54 in the solution 31 contained in the predetermined region 1, and is incident on the imaging unit 41 of the imaging device 4 to form an image. The imaging unit 41 captures an image of the composite particles 54 collected in the predetermined region 1 where the spatial light is incident. The imaging unit 41 has a function of capturing an object and acquiring an image. As the imaging unit 41, for example, it is possible to use an image capturing device such as a camera or a video camera that captures a still image or a moving image. FIG. 4 shows an example of an image 100 in the predetermined region in the solution imaged by the imaging unit 41 constituting the detection device 101 of the substance to be measured according to the first embodiment of the present disclosure.

The detection unit 42 of the imaging device 4 detects the composite particles 54 based on the image 100 captured by the imaging unit 41. The detection unit 42 detects the composite particles 54 from an image including the composite particles 54 and the unreacted magnetic labeling substances 53 collected in the predetermined region 1 as the detection region. In particular, the image of the magnetic labeled composite particles 54 collected on the upper surface of the container 3 is analyzed by its shape, brightness, and movement due to magnetic field or convection. Although the unreacted magnetic labeling substance 53 and the composite particles 54 are mixed at the upper surface of the solution 31, they can be distinguished each other based on the shape of the substance to be measured 51 and that the substance to be measured 51 and the magnetic labeling substance 53 are combined.

The control unit 43 of the imaging device 4 controls the imaging device 4 entirely. Further, the control unit 43, if necessary, controls units and devices other than the imaging device 4 included in the detection device 101.

As the imaging device 4, for example, it is possible to use a computer or the like having a CPU and a memory. A function of the detection unit 42 detecting the composite particles 54 from the image 100 captured by the imaging unit 41 and a function of the control unit 43 are performed by the PC in the imaging device 4 according to a program stored in advance in the memory in the imaging device 4. The imaging unit 41, the detection unit 42, and the control unit 43 need not necessarily be realized by one computer or the like, and may be realized by a plurality of computers or the like.

The magnetic labeling substance 53 specifically binds to the substance to be measured 51. The magnetic labeling substance 53 does not bind to the other substance 52. As shown in FIG. 1, since the composite particles 54 is the material to be measured 51 coupled with the magnetic labeling substance 53, the composite particles 54 moves toward a direction of an arrow A by the effect of the magnetic field applied by the magnetic field applying unit 2. On the other hand, since the other substances 52 do not include the magnetic labeling substance 53, they settles to the lower region of the container 3 by the gravitational force acting in the downward direction of the container 3 as indicated by the arrow B. Therefore, the composite particles 54 are collected in the predetermined region 1 other than the lower region of the container 3 by the magnetic field applied by the magnetic field applying unit 2. The spatial light is incident on the predetermined region 1, and reflected light, transmitted light, and the scattered light or the like from the predetermined region 1 are imaged by the imaging unit 41, so that it is possible to obtain an image including the composite particles 54.

Figure 5:
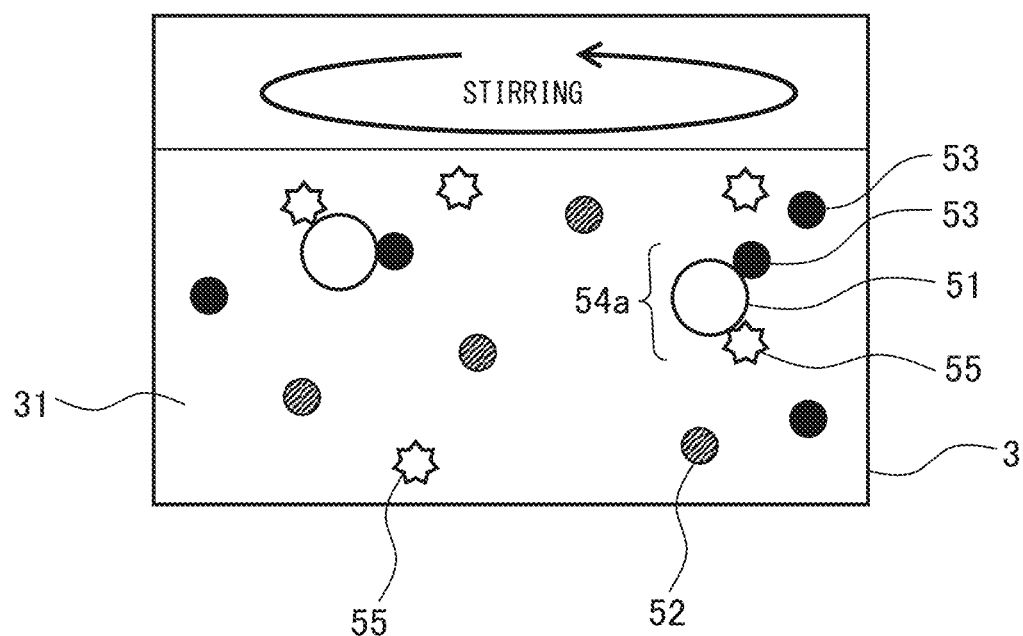
FIG. 5 is a side view of the container constituting the detection device of the substance to be measured according to the first embodiment of the present disclosure showing a state where a substance to be measured, a magnetic labeling substance and a fluorescent labeling substance are put into the solution, and showing reaction between them is accelerated by stirring.

Further, if the substance having optical characteristics, such as a fluorescent labeling substance, is also labeled, the S/N ratio can be improved. FIG. 5 is a side view of the container 3 constituting the detection device 101 of the substance to be measured according to the first embodiment of the present disclosure, which shows a state of providing the substance to be measured 51, the magnetic labeling substance 53 and the fluorescent labeling substance 55 in the solution 31 and accelerating the reaction by stirring them. When the fluorescent labeling substance 55 has a property of specifically binding to the substance 51 to be measured, the solution 31 containing the substance 51 to be measured, the magnetic labeling substance 53, and the fluorescent labeling substance 55 is stirred, so that a composite particle 54a in which the magnetic labeling substance 53 and the fluorescent labeling substance 55 are bound to the substance 51 to be measured can be formed.

Applying a magnetic field to the solution 31 and providing the magnetic field applying unit 2 in the upper portion of the container 3 as shown in FIG. 1, the composite particles 54a (not shown) can be collected in the predetermined region 1 other than the lower region of the container 3. On the other hand, the other substances 52 settle by gravity and are collected in the lower region of the container 3.

Figure 6:
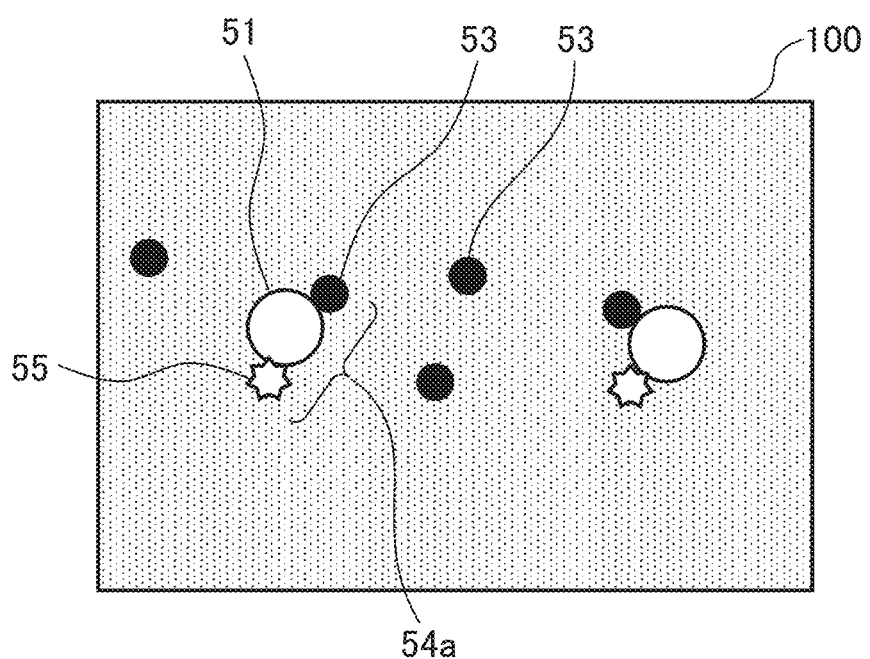
FIG. 6 is another example of an image in the predetermined region in the solution captured by the imaging unit constituting the detection device of the substance to be measured according to the first embodiment of the present disclosure.

FIG. 6 shows another example of an image in the predetermined region 1 in the solution 31 captured by the imaging unit 41 constituting the detection device 101 of the substance to be measured according to the first embodiment of the present disclosure. The image 100 in the predetermined region 1 captured by the imaging unit 41 includes an image of the composite particles 54a and the magnetic labeling substance 53 collected by the magnetic field applying unit 2, but the other substances 52 are not included. Further, since the composite particles 54a include the fluorescent labeling substance 55, observation of the composite particles 54a can be easily performed by irradiating the predetermined region 1 with fluorescence.

As described above, according to the detection device of the substance to be measured according to the first embodiment, since the respective spatial positions of the composite particles in which the magnetic labeling substance is bound to the substance to be measured and the other substances other than the substance to be measured are separated and the composite particles are detected by using the spatial light, the substance to be measured can be easily detected.

Second Embodiment

Figure 7:
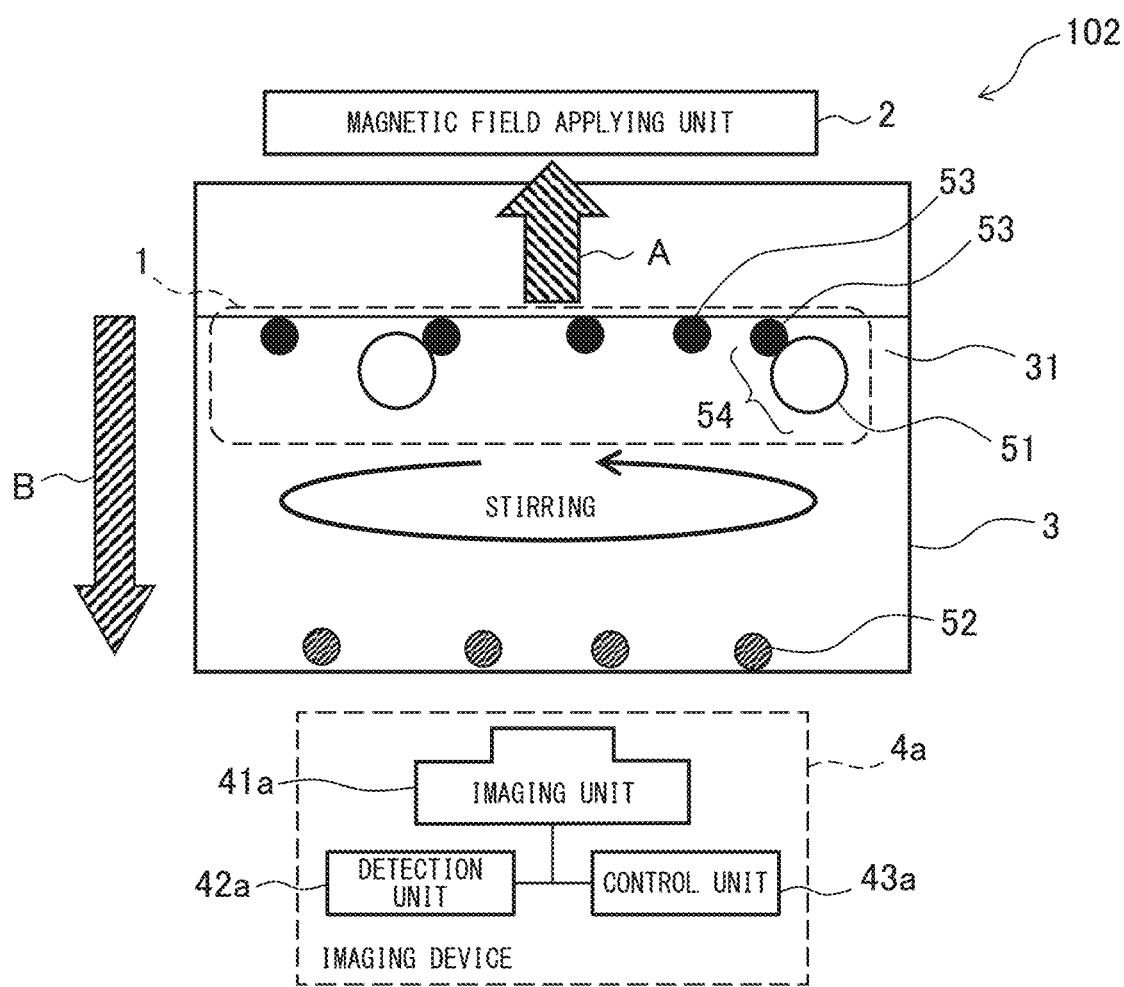
FIG. 7 is a configuration diagram of a detection device of the substance to be measured according to a second embodiment of the present disclosure.

Next, a detection device of the substance to be measured according to a second embodiment of the present disclosure will be described. FIG. 7 shows a configuration diagram of a detection device 102 of the substance to be measured according to the second embodiment of the present disclosure. The difference between the detection device 102 of the substance to be measured according to the second embodiment and the detection device 101 of the substance to be measured according to the first embodiment is a point where the magnetic field applying unit 2 is disposed above the container 3, and the imaging unit 41a is disposed below the container 3. Other configurations of the detection device 102 of the substance to be measured according to the second embodiment are the same as those of the configuration of the detection device 101 of the substance to be measured according to the first embodiment, and therefore, a detailed description thereof will be omitted.

As in the case of the first embodiment, the magnetic field applying unit 2 in the second embodiment is disposed above the container 3. Due to the magnetic field gradient generated by the magnetic field applying unit 2 in the direction of the arrow A, the composite particle 54 in which the magnetic labeling substance 53 is bound to the substance to be measured 51 and the unreacted magnetic labeling substance 53 move to the upper portion of the container 3, and are collected in the predetermined region 1 other than the lower region of the container 3. On the other hand, the other substance 52 to which the magnetic labeling substance 53 is not bound is settled by gravity toward the direction of the arrow B, and is collected in the lower region of the container 3.

On the other hand, unlike the case of the first embodiment, in the second embodiment, the imaging device 4a including the imaging unit 41a, the detection unit 42a, and the control unit 43a is disposed below the container 3. When the imaging unit 41a captures an image of a predetermined area 1, it is possible to perform capturing the image without being blocked by the magnetic field applying unit 2. Incidentally, the imaging unit 41a is to image the predetermined region 1 over the lower region of the container 3 (bottom surface), it is considered that the other substance 52 does not interfere with imaging when the amount of the other substance 52 is small.

Further, as shown in FIG. 7, by moving the other substance 52 to the side of the container 3 by stirring, without being hindered by the other substance 52, the imaging unit 41a may be capable of capturing an image of the composite particles 54. Thus, an effect is obtained in which the other substance 52 is exhaled from the detection region by stirring.

Further, FIG. 7 shows an example in which the imaging unit 41a is disposed below the container 3 (bottom side) and is not limited by such an example, the imaging unit 41a may be disposed on the side surface side of the container 3. With such a configuration, the imaging unit 41a can capture an image of the predetermined region 1 including the composite particles 54 without being affected by the other substances 52 collected on the bottom surface of the container 3.

Third Embodiment

Figure 8:
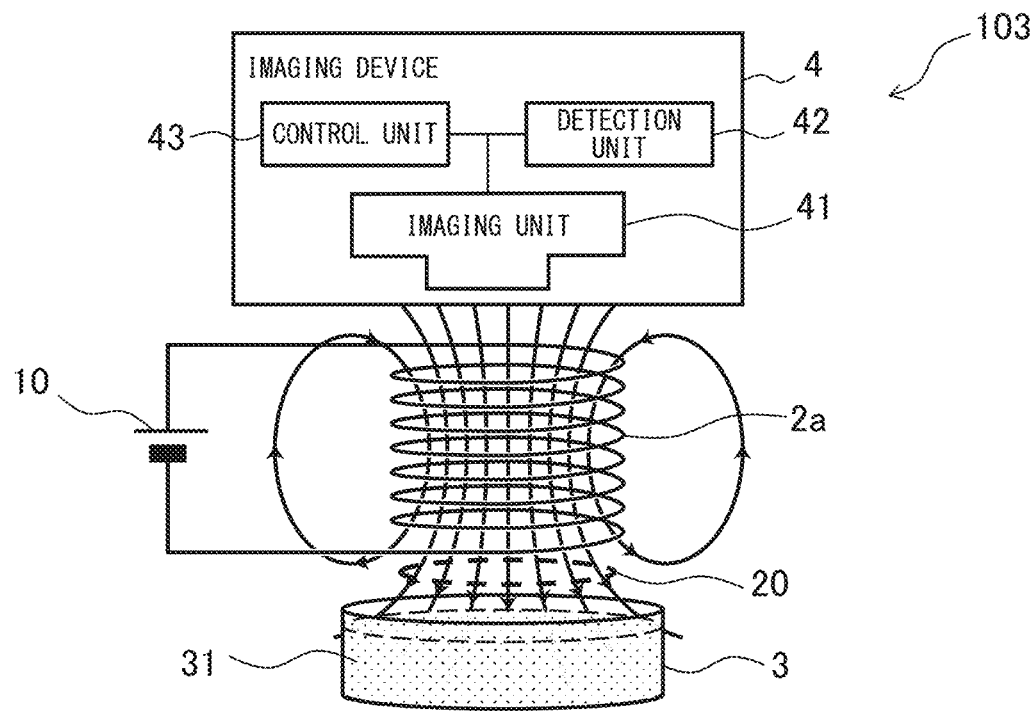
FIG. 8 is a configuration diagram of a detection device of the substance to be measured according to a third embodiment of the present disclosure.

Next, a detection device of the substance to be measured according to a third embodiment of the present disclosure will be described. FIG. 8 shows a configuration diagram of a detection device 103 of the substance to be measured according to the third embodiment of the present disclosure. The difference between the detection device 103 of the substance to be measured according to the third embodiment and the detection device 101 of the material to be measured according to the first embodiment is a point where the magnetic field applying unit has a first coil 2a and the imaging unit 41 is arranged at a position facing to the container 3 across the first coil 2a, so that it is possible to image the inside of the container 3 through the first coil 2a. Since other configurations of the detection device 103 of the substance to be measured according to the third embodiment are the same as those of the configuration of the detection device 101 of the substance to be measured according to the first embodiment, a detailed description thereof will be omitted.

The magnetic field applying unit constituting the detection device 103 of the substance to be measured according to the third embodiment of the present disclosure has the first coil 2a and a DC power supply 10. When the first coil 2a is connected to the DC power source 10 and current flows through the first coil 2a, a magnetic field 20 is generated in the first coil 2a and the magnetic field is applied to the container 3. The solution 31 of the container 3 contains the composite particles which is the substance to be measured bound with the magnetic labeling substance, the unreacted magnetic labeling substance, and the other substances. By the magnetic field 20, the magnetic labeling substance contained in the solution 31 in the container 3 can be collected in the predetermined region other than the lower region of the container 3.

The imaging unit 41 is arranged at a position facing the container 3 across the first coil 2a, so that it is possible to capture an image of the inside of the container 3 through the inner side of the first coil 2a. In the case a magnet or the like is provided on the upper surface of the container 3, when capturing an image of the predetermined area 1 in the container 3, it is necessary to move the magnet or the like, since the magnet blocks a predetermined area. In contrast, by providing the air-core portion of the air-core coil such as the first coil 2a on the upper surface of the solution 31, the imaging unit 41 is capable of capturing an image of the predetermined region from above while applying a magnetic field.

Figure 9:
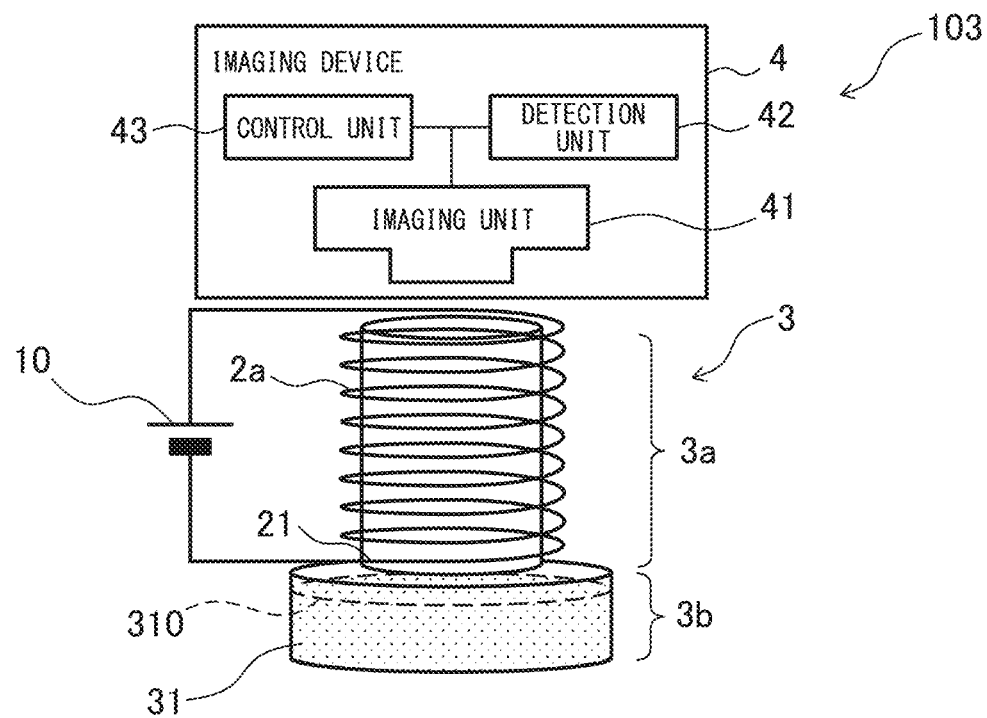
FIG. 9 is a configuration diagram of a modified example of the detection device of the substance to be measured according to the third embodiment of the present disclosure.

FIG. 9 shows a configuration diagram of a modified example of the detection device 103 of the substance to be measured according to the third embodiment of the present disclosure. As shown in FIG. 9, the container 3 has a structure divided into an upper container 3a wound by the first coil 2a and a lower container 3b containing the solution 31. With such a configuration, the first coil 2a can be stably disposed above the container 3. The upper container 3a and the lower container 3b may be integrally formed or may be separable. However, so that the solution 31 can be observed from the imaging unit 41, it is preferable that the upper container 3a is composed of a transparent material or a hollow structure.

It is preferable that the upper container 3a does not contain the solution 31. It is preferable that a lower end portion 21 of the first coil 2a and a liquid level 310 of the solution 31 are arranged at a predetermined interval. This is because the magnetic field generated by the first coil 2a becomes stronger as it is closer to the wire constituting the first coil 2a, so if the liquid surface 310 of the solution 31 becomes too close to the lower end portion 21 of the first coil 2a and the composite particles coupled with the magnetic labeling substance will be attracted and concentrated at the vicinity of the wire, and the density of the composite particles in the region observed through the hollow portion of the first coil 2a becomes low, which makes it difficult to observe the composite particles. By arranging the lower end portion 21 of the first coil 2a and the liquid level 310 of the solution 31 at a predetermined interval, it is possible to avoid the density of the composite particles from becoming non-uniform in the region observed through the hollow portion of the first coil 2a, and it is possible to easily observe the composite particles.

Figure 10:
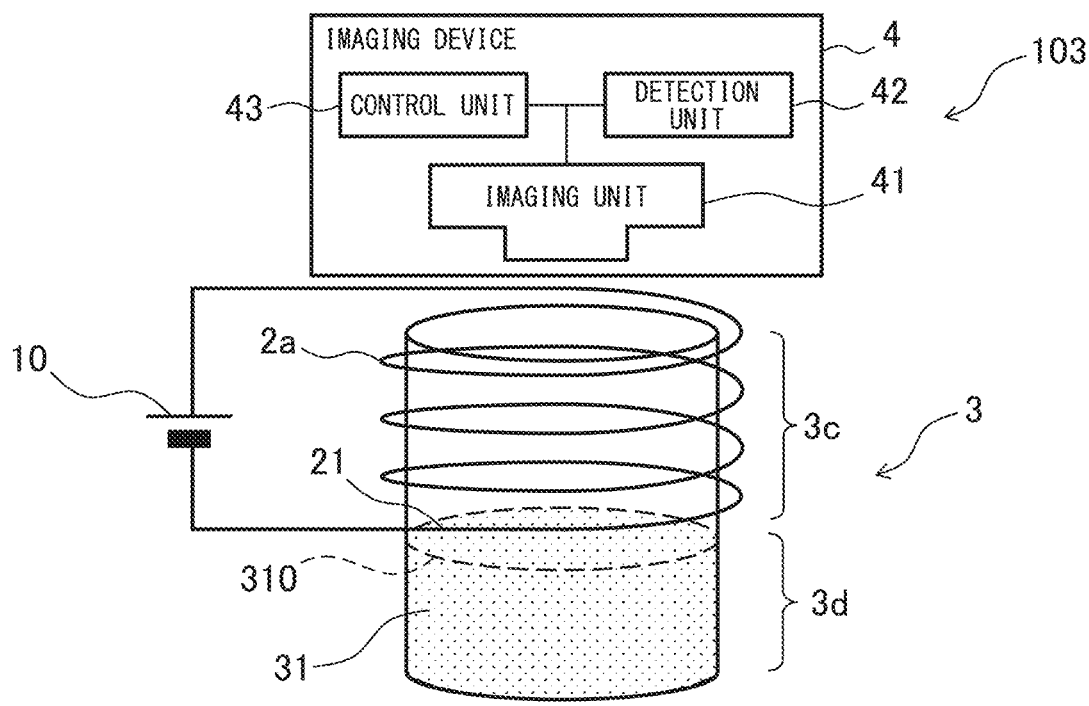
FIG. 10 is a configuration diagram of another modified example of the detection device of the substance to be measured according to the third embodiment of the present disclosure.

FIG. 10 shows a configuration diagram of another modified example of the detection device 103 of the substance to be measured according to the third embodiment of the present disclosure. As shown in FIG. 10, the container 3 is divided into a first portion 3c wound by the first coil 2a and a second portion 3d containing the solution 31, and the first portion 3c and the second portion 3d has a continuous integral structure. With such a configuration, it is possible to stably arrange the first coil 2a on the solution 31 with a simple structure. For the same reason as described above, it is preferable that the lower end portion 21 of the first coil 2a and the liquid level 310 of the solution 31 be arranged at a predetermined interval.

Fourth Embodiment

Figure 11:
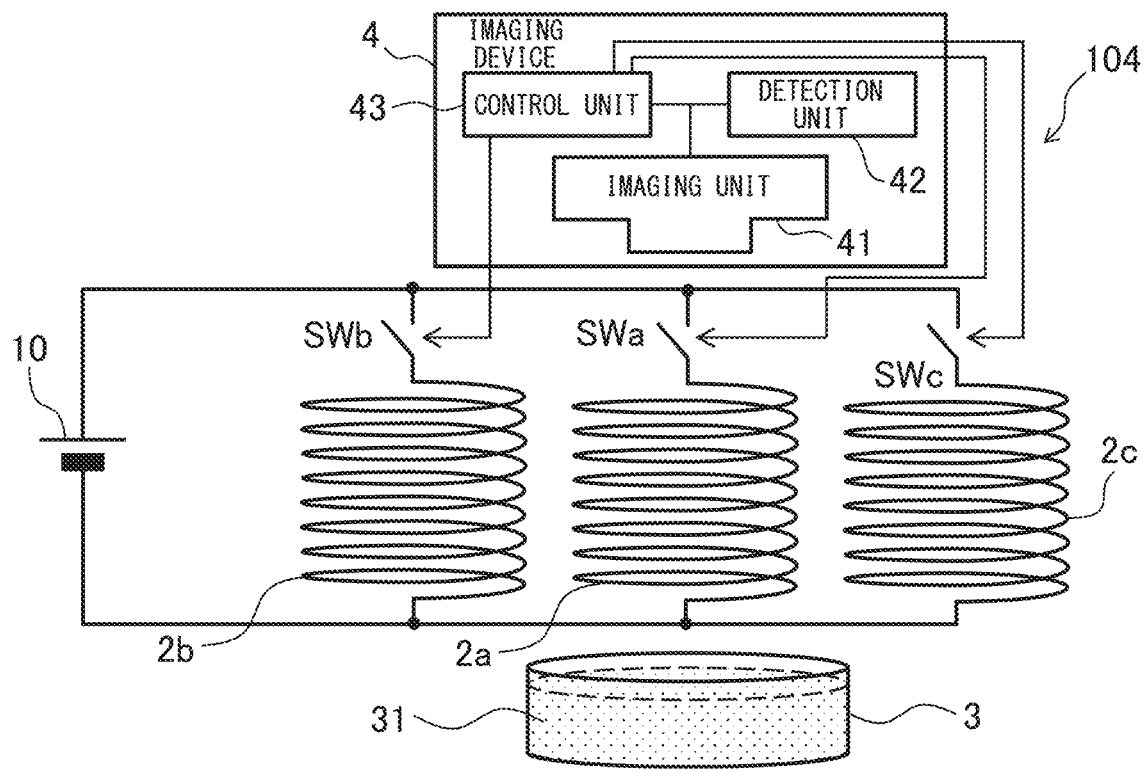
FIG. 11 is a configuration diagram of a detection device of the substance to be measured according to a fourth embodiment of the present disclosure.

Next, a detection device of the substance to be measured according to a fourth embodiment of the present disclosure will be described. FIG. 11 shows a configuration diagram of a detection device 104 of the substance to be measured according to the fourth embodiment of the present disclosure. The difference between the detection device 104 of the material to be measured according to the fourth embodiment and the detection device 103 of the material to be measured according to the third embodiment is a point where the magnetic field applying unit further has a second coil 2b and the second coil 2b is arranged at a position such that the magnetic field can be applied to a different position from the position where the magnetic field is applied by the first coil 2a. Since other configurations of the detection device 104 of the substance to be measured according to the fourth embodiment are the same as those of the configuration of the detection device 103 of the substance to be measured according to the third embodiment, a detailed description thereof will be omitted.

As shown in FIG. 11, the first coil 2a is disposed above the container 3, so that the magnetic field can be applied to a position different from the position where the magnetic field is applied by the first coil 2a, the second coil 2b and the third coil 2c are disposed at a position facing each other across the first coil 2a. The solution 31 of the container 3 contains the composite particles which is the substance to be measured bound with the magnetic labeling substance, the unreacted magnetic labeling substance, and the other substances. The first to third coils (2a, 2b, 2c) are connected with switches (SWa, SWb, SWc) in series, respectively, and it is possible to turn on/off the connection to the DC power supply 10, individually.

The control unit 43 controls the operation of the switches SWa, SWb, and SWc. The switches SWa, SWb, and SWc may be configured so that the user of the detection device 104 can control the operation of the switches SWa, SWb and SWc. In this case, the user can directly control the switches SWa, SWb, and SWc.

Figure 12:
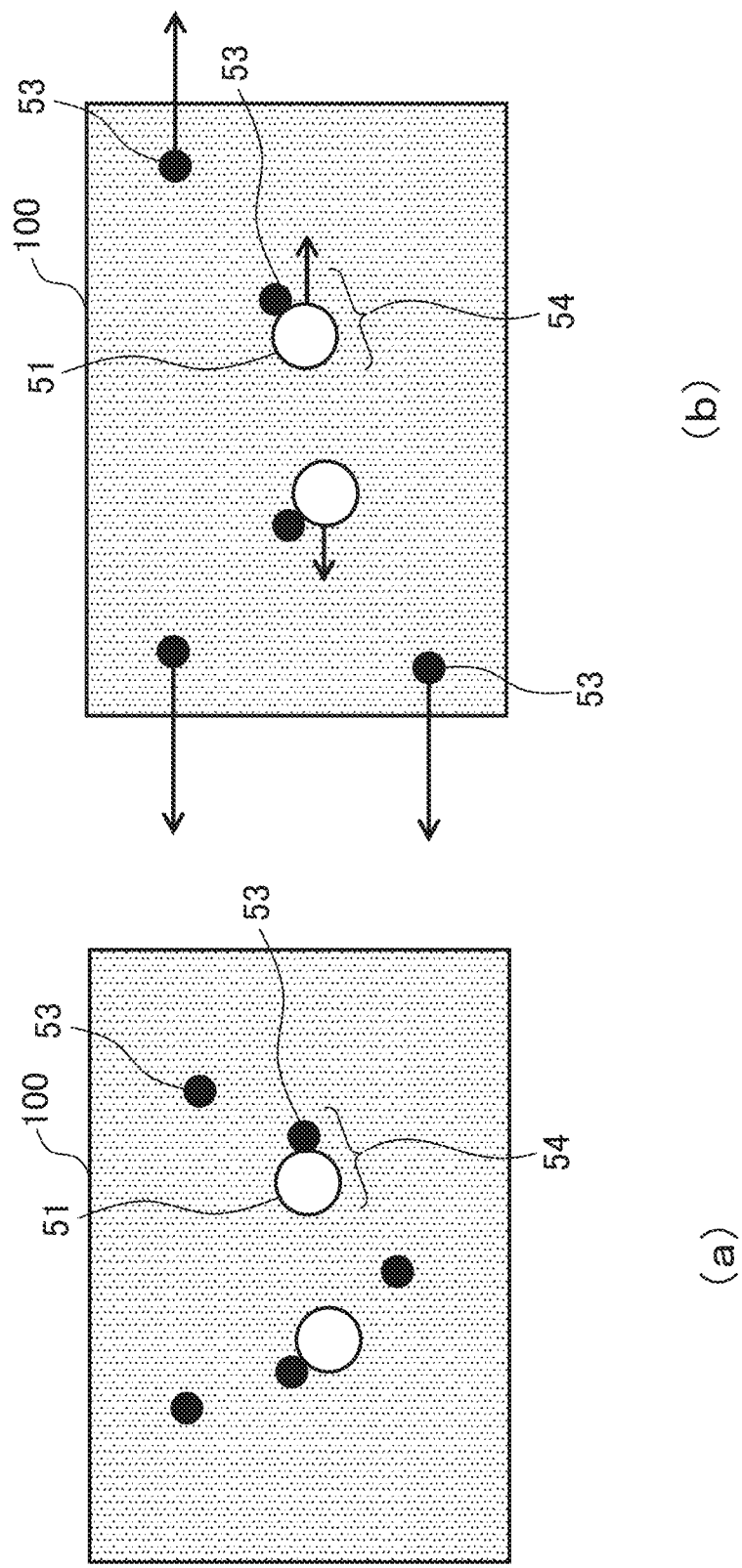

First, the switch SWa is turned on, and a current is applied only to the first coil 2a. A magnetic field is applied to the predetermined region in the solution 31 of the container 3, and the composite particles and the magnetic labeling substance are collected in the predetermined region. FIG. 12 (a) is an image in the predetermined region in the solution 31 captured by the imaging unit 41 constituting the detection device 104 of the substance to be measured according to the fourth embodiment of the present disclosure, showing an image 100 when a magnetic field is applied to the predetermined region only by the first coil 2a. Within the image 100, the composite particles 54 and the magnetic labels 53 are included.

When the first coil 2a is provided on the upper surface of the container 3, the unreacted magnetic labeling substance 53 and the composite particles 54 will aggregate in a region where a magnetic flux density is high. Therefore, S/N loss may occur, since the composite particles 54 are missing in the unreacted magnetic labeling substance 53.

Therefore, in this embodiment, after collecting the magnetic labeling substance 53 and the composite particles 54 in the predetermined region, the region where the magnetic field is applied is moved so as to loosen the aggregation of the unreacted magnetic labeling substance 53 and the composite particles 54.

Next, when the switch SWa is turned off and the switches SWb and SWc are turned on, the application of the magnetic field from the first coil 2a is eliminated, the magnetic field is applied to the predetermined region of the solution 31 from the second coil 2b and the third coil 2c. FIG. 12 (b) shows an image 100 of the predetermined area when stopping the application of the magnetic field by the first coil 2a and applying a magnetic field to the predetermined area by the second coil 2b and the third coil 2c. While the application of the direction field by the first coil 2a is stopped, the composite particles 54, and the unreacted magnetic labeling substance 53 which is not coupled with the substance to be measured 51 move away from the center of the container 3 as indicated by the direction of arrow in FIG. 12 (b) by the magnetic field applied by the second coil 2b and the third coil 2c. At this time, since the unreacted magnetic labeled substance 53 is lighter than the composite particles 54, it moves faster than the composite particles 54. As a result, only the unreacted magnetic labeled substance 53 can be excluded from the predetermined region which is an observation region, and a large number of the composite particles 54 remain in the predetermined region, so that the shape, brightness, and movement of the composite particles 54 can be easily captured, and the S/N ratio can be improved.

Figure 13:
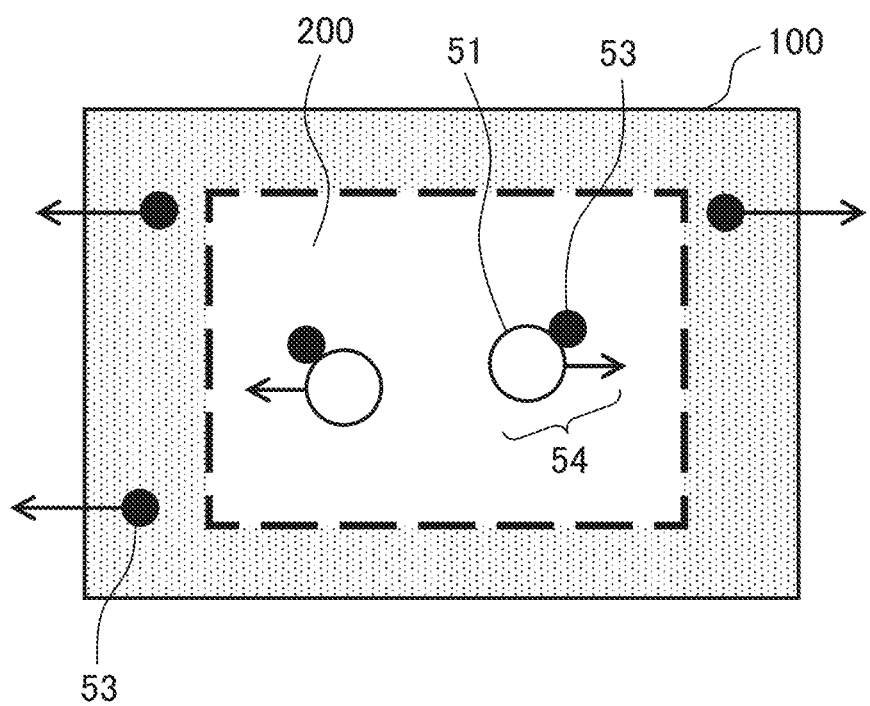
FIG. 13 is another example of an image in the predetermined region in the solution imaged by the imaging unit constituting the detection device of the substance to be measured according to the fourth embodiment of the present disclosure.

FIG. 13 shows another example of an image in the predetermined region in the solution 31 imaged by the imaging unit 41 constituting the detection device 104 of the substance to be measured according to the fourth embodiment of the present disclosure. As shown in FIG. 13, by setting a specific region 200 in which the density of the unreacted magnetic labeling substance 53 is lowered inside the image 100, an image having a high density of the composite particles 54 can be obtained.

In the detection device 104 of the substance to be measured according to the fourth embodiment of the present disclosure, for example, the image 100 is captured by the following control.

(First step) The switch SWa is turned on and the switches SWb and SWc are turned off by the control of the control unit 43, so as to start applying the magnetic field by the first coil 2a and wait for a predetermined time (first predetermined time).

(Second step) After the first predetermined time has elapsed, under the control of the control unit 43, the switch SWa is turned off and the switches SWb and SWc are turned on, so as to stop the applying the magnetic field by the first coil 2a, and start applying the magnetic field by the second coil 2b and the third coil 2c, and to wait for a predetermined time (second predetermined time).

(Third step) After the second predetermined time has elapsed since the start of the applying the magnetic field by the second coil 2b and the third coil 2c, the imaging unit 41 captures the image 100 by the control of the control unit 43.

For example, the specific region 200 is predetermined as follows. In other words, in the state of the third step, the specific region 200 is predetermined so that only the composite particles 54 are contained in the specific region 200 and the unreacted magnetic labeling substance 53 is moved outside the specific region 200. Since the unreacted magnetic labeled substance 53 is lighter than that of the composite particles 54 and the migration rate is faster than that of the composite particles 54, it is possible to define the specific region 200 in this manner. The first and second predetermined time and the specific region 200 can be set in advance in an experiment or the like.

The detection unit 42 (imaging device 4) performs a process of detecting the composite particles 54 only in the predetermined specific area 200 included in the image 100. The imaging unit 41 may capture an image so that only the specific region 200 is captured.

Since only the composite particles 54 are present in the specific region 200, it is possible to realize simplification and speeding up of the processing and improvement of detection accuracy.

Although FIG. 11 shows an example in which the second coil 2b and the third coil 2c are provided, only the second coil 2b may be arranged. Further, although an example in which the second coil 2b and the third coil 2c are air-core coil has been shown, the present invention is not limited to such an example, and an iron-core coil may be used. Alternatively, the applying the magnetic field by the first coil 2a may be stopped, and at the same time, a permanent magnet or the like may be arranged at a position facing each other across the first coil 2a.

Fifth Embodiment

Figure 14:
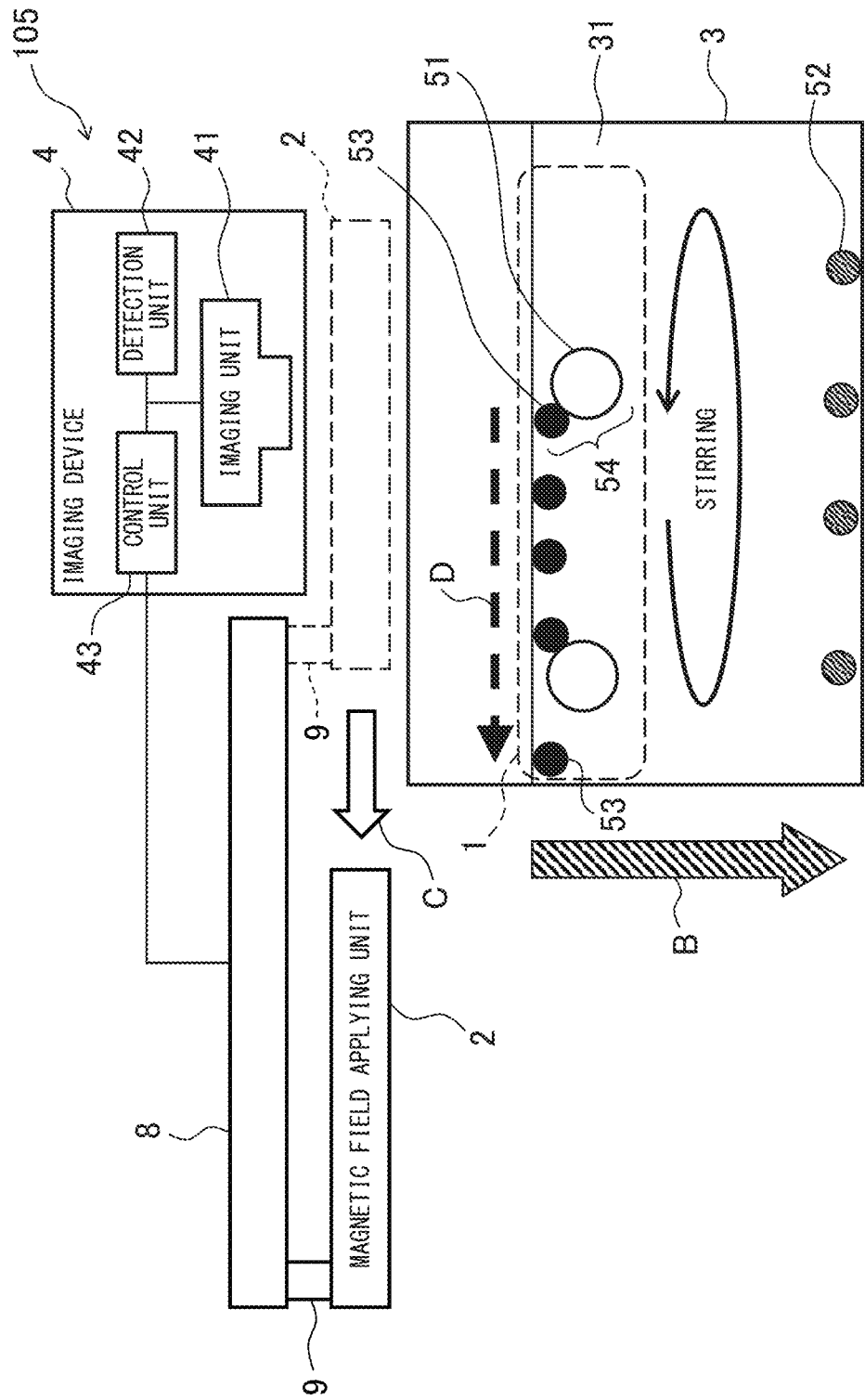
FIG. 14 is a configuration diagram of a detection device of the substance to be measured according to a fifth embodiment of the present disclosure.

Next, a detection device of the substance to be measured according to a fifth embodiment of the present disclosure will be described. FIG. 14 shows a configuration diagram of a detection device 105 of the substance to be measured according to a fifth embodiment of the present disclosure. The difference between the detection device 105 of the substance to be measured according to the fifth embodiment and the detection device 101 of the material to be measured according to the first embodiment is a point where the imaging unit 41 is arranged at a position facing the container 3 with the magnetic field applying unit 2 interposed therebetween, and the magnetic field applying unit 2 moves relative to the container 3 to a position that does not interfere with imaging by the imaging unit 41 when the imaging unit 41 captures an image. Since other configurations of the detection device 105 of the substance to be measured according to the fifth embodiment are the same as those of the configuration of the detection device 101 of the substance to be measured according to the first embodiment, a detailed description thereof will be omitted.

In the detection device 105 according to the fifth embodiment, after collecting the unreacted magnetic labeling substance 53 and the composite particles 54 by arranging a magnet which is the magnetic field applying unit 2 on the upper surface of the container 3, the magnet which is the magnetic field applying unit 2 moves relative to the container 3 to secure the observation area, and enable observation from the upper surface of the container 3. That is, the container 3 and the imaging device 4 may be fixed the magnet which is the magnetic field applying unit 2 may be moved with respect to the container 3, or the magnet which is the magnetic field applying unit 2 may be fixed, and the container 3 and the imaging device 4 may be moved with respect to the magnetic field applying unit 2. Alternatively, the magnet which is the magnetic field applying unit 2, and the container 3 and the imaging device 4 may be moved in opposite directions to each other. The process until the magnetic field is applied to the upper surface of the solution 31 by the magnetic field applying unit 2 is the same as that in the first embodiment.

As a moving mechanism of the magnet which is the magnetic field applying unit 2 will be described with reference to three examples. In the following description, a case where the container 3 and the imaging device 4 are fixed and the magnet which is the magnetic field applying unit 2 is moved with respect to the container 3 will be described as an example. However, the magnet which is the magnetic field applying unit 2 may be fixed, and the container 3 and the imaging device 4 may be moved with respect to the magnetic field applying unit 2, or the magnet which is the magnetic field applying unit 2, the container 3 and the imaging device 4 may be moved in opposite directions to each other. The detection device according to the first example, as shown in FIG. 14, has a drive unit (driver) 8 which can slide the magnetic field applying unit 2 in the horizontal direction through a connecting portion 9. First, the magnetic field applying unit 2 is arranged at a position shown by a dotted line in FIG. 14 to collect the composite particles 54 and the unreacted magnetic labeling substance 53 on the upper surface of the solution 31 by a magnetic field gradient. Thereafter, the magnetic field applying unit 2 is moved horizontally as indicated by the direction of arrow C by controlling the drive unit 8 by the control unit 43. Then, since the magnetic field applying unit 2 which has been disposed between the imaging unit 41 and the predetermined region 1 is moved, the imaging unit 41 can directly image the predetermined region 1. At this time, with the movement of the magnetic field applying unit 2, so that the composite particles 54 and the unreacted magnetic labeling substance 53 move to the direction of the dotted line arrow D by the magnetic field from the magnetic field applying unit 2, it is preferable to bring the magnetic field applying unit 2 close to the solution 31. This is because if the distance between the magnetic field applying unit 2 and the solution 31 is too large, the magnetic field from the magnetic field applying unit 2 becomes too weak, and the composite particles 54 and unreacted magnetic labeling substance 53 are sedimented by gravity and it becomes difficult to separate from the other substance 52.

Figure 15:
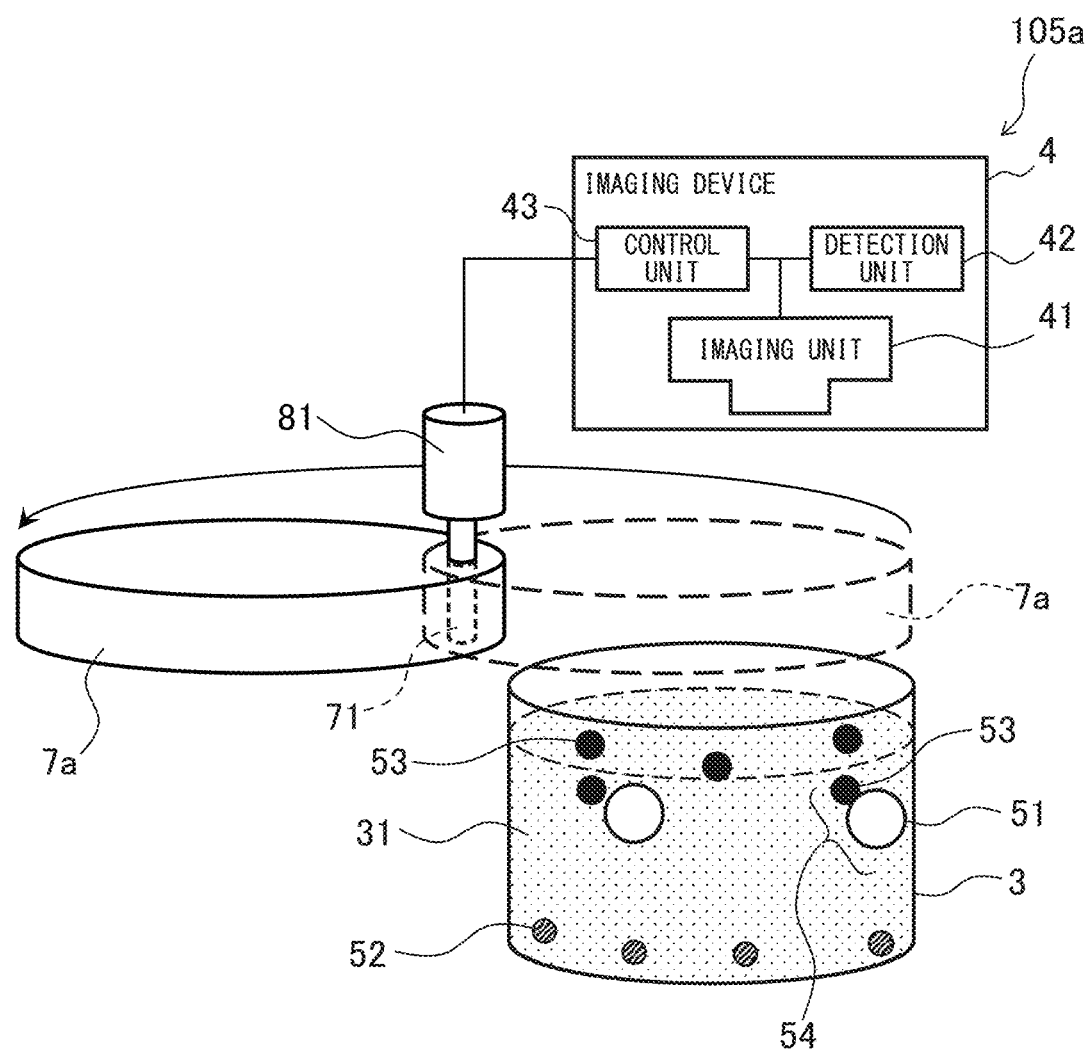
FIG. 15 is a configuration diagram of a modified example of the detection device of the substance to be measured according to the fifth embodiment of the present disclosure.

The detection device according to the second example has a configuration for rotating and moving a magnet is the magnetic field applying unit about a rotation axis. FIG. 15 is a configuration diagram of a second example of a modified example 105a of the detection device of the substance to be measured according to the fifth embodiment of the present disclosure. An end portion of the magnet 7a which is a magnetic field applying unit is pivotally supported by a rotary shaft 71 which is driven to rotate by the driving unit 81. By controlling the drive unit 81 by the control unit 43, the rotation shaft 71 is rotated, and it is possible to rotate the magnet 7a about the rotation shaft 71. As shown by the dotted line in FIG. 15, the magnet 7a is disposed on the upper part of the container 3 in the state before rotation. At this time, a magnetic field is applied from the magnet 7a, the composite particles 54 which is the substance to be measured 51 bound with magnetic labeling substance 53 and the unreacted magnetic labeling substance 53 is collected on the upper surface portion of the solution 31. On the other hand, the other substance 52 precipitates on the bottom surface of the container 3 due to the influence of gravity. Since the magnet 7a is disposed between the imaging unit 41 and the container 3 in this state, the imaging unit 41 can not capture an image of the upper surface portion of the solution 31.

Next, the control unit 43 controls the drive unit 81 to rotate the magnet 7a about the rotation shaft 71 and to move the magnet 7a to the position shown by the solid line in FIG. 15. In this state the magnet 7a is no longer disposed between the imaging unit 41 and the container 3, the imaging unit 41 is capable of capturing an image of the upper surface portion of the solution 31.

However, when the magnet 7a is moved from the upper portion of the container 3 to a position where the magnetic field is not applied to the upper surface portion of the solution 31, the composite particles 54 start to settle due to the influence of gravity. Therefore, it is preferable that the magnet 7a is placed in the vicinity of the container 3 so that capturing by the imaging unit 41 is not prevented and the magnetic field such that the composite particles 54 do not settle is applied to the upper surface portion of the solution 31. In this way, it is possible to suppress sedimentation due to gravity of the composite particles 54 to a certain extent while allowing the imaging unit 41 to capture an image of the predetermined region.

Figure 16:
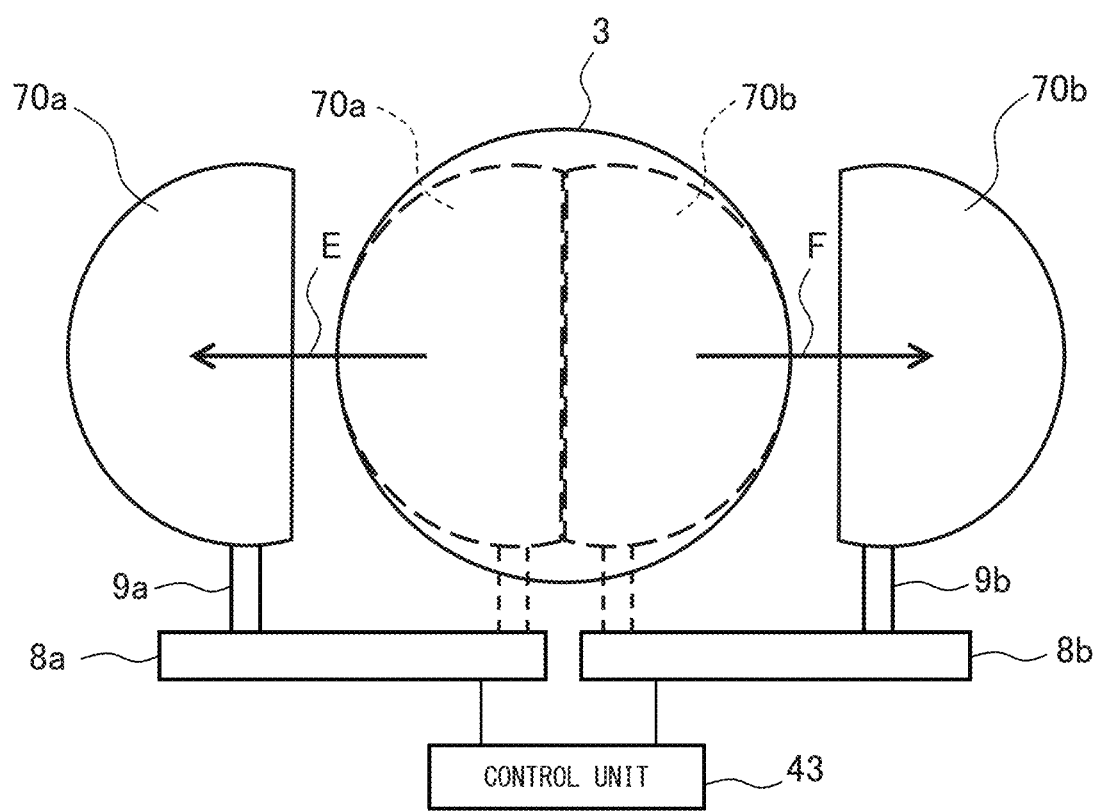
FIG. 16 is a plan view showing another modified example of the magnetic field applying unit constituting the detection device of the substance to be measured according to the fifth embodiment of the present disclosure.

The detection device according to the third example has a configuration that a plurality the magnet which is a magnetic field applying unit is disposed on the solution top surface, and disposed around the observation area, i.e. on the outer peripheral region of the solution top surface at the time of observation. FIG. 16 shows a plan view of a magnetic field applying unit constituting the third example which is another modified example of the detection device of the substance to be measured according to the fifth embodiment of the present disclosure. FIG. 16 is a view of the magnets 70a and 70b which are magnetic field applying units and the container 3 taken from above the container 3, and the imaging unit is not illustrated. The magnets 70a and 70b are connected to the drive unit 8a and 8b via the connecting portions 9a and 9b, respectively. The drive units 8a and 8b have a mechanism capable of sliding the magnets 70a and 70b in the horizontal direction.

First, as shown by the dotted line in FIG. 16, the magnets 70a and 70b which are the magnetic field applying unit are arranged on the upper surface portion of the container 3 to collect the composite particles to the upper surface portion of the solution. Since the magnets 70a and 70b are disposed between the imaging unit and the container 3 in this state, the imaging unit can not capture the image of the upper surface portion of the solution.

Next, as shown by the directions of arrows E and F in FIG. 16, the control unit 43 controls the drive units 8a and 8b via the connecting portions 9a and 9b to move the magnets 70a and 70b in the horizontal direction away from the container 3. The magnets 70a and 70b are not disposed between the imaging unit and the container 3 in this state, the imaging unit becomes possible to directly capture the image of the upper surface portion of the solution.

However, when the magnets 70a and 70b are moved from the upper part of the container 3 to a position where a magnetic field is not applied to the upper surface portion of the solution, the composite particles start to settle due to the influence of gravity. Therefore, it is preferable to arrange the magnets 70a and 70b in the vicinity of the container 3 so that capturing by the imaging unit is not hindered and the magnetic field is applied to the upper surface portion of the solution to such an extent that the composite particles do not settle. In this way, since the magnetic field from the magnets 70a and 70b is applied to the upper surface portion of the solution, it is possible to suppress the settling due to the gravitational force of the composite particles to a certain extent.

Sixth Embodiment

Figure 17:
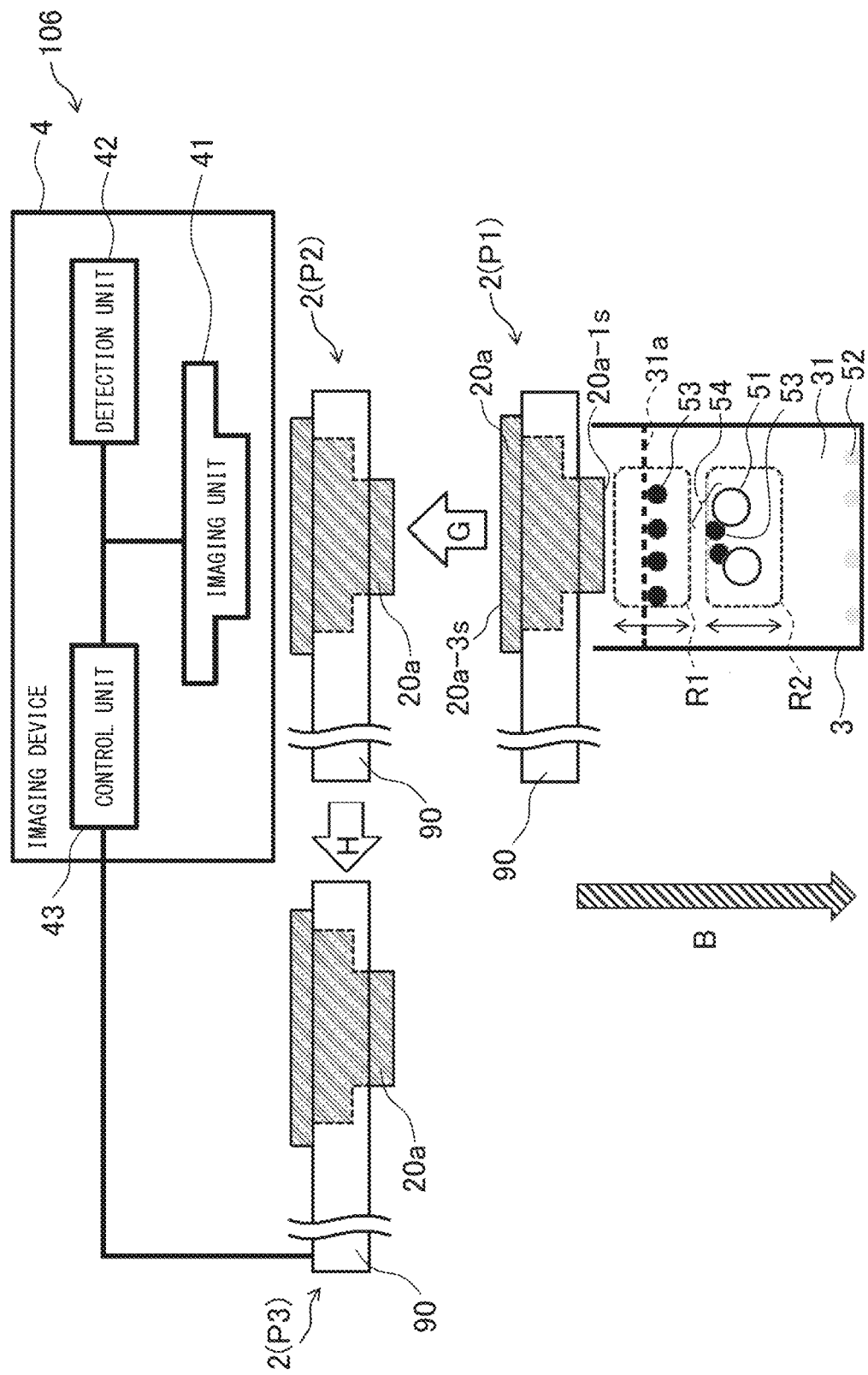
FIG. 17 is a configuration diagram of a detection device of the substance to be measured according to a sixth embodiment of the present disclosure.

Next, a detection device of the substance to be measured according to a sixth embodiment of the present disclosure will be described. FIG. 17 shows a configuration diagram of a detection device 106 of the substance to be measured according to the sixth embodiment of the present disclosure. The difference between the detection device 106 of the substance to be measured according to the sixth embodiment and the detection device 101 of the substance to be measured according to the first embodiment is a point where the magnet 20a constituting the magnetic field applying unit 2 includes the first plane member (20a-1s) opposed to the upper surface 31a of the solution 31 and the second plane member (20a-3s) opposed to the imaging unit 41, and the area of the first plane member (20a-1s) is smaller than the area of the second plane member (20a-3s). Since other configurations of the detection device 106 of the substance to be measured according to the sixth embodiment are the same as those of the configurations of the detection device 101 of the substance to be measured according to the first embodiment, a detailed description thereof will be omitted.

Figure 18:
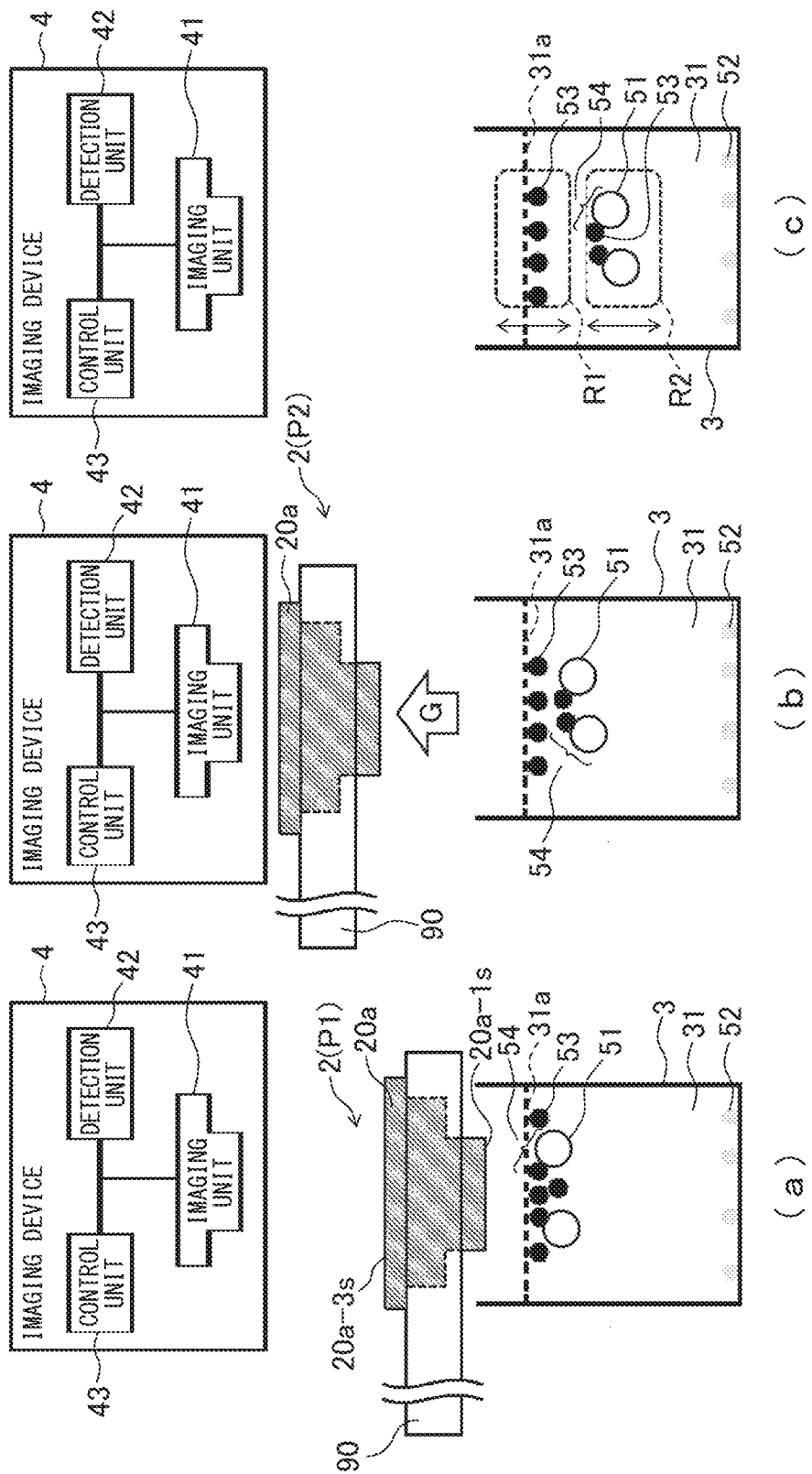
FIGS. 18(a) to 18(c) are diagrams for explaining a detection procedure by the detection device of the substance to be measured according to the sixth embodiment of the present disclosure.

In the detection device 106 of the substance to be measured according to the sixth embodiment, as described later, the magnetic field applying unit 2 includes a magnet 20a and a holder 90 for holding the magnet 20a. FIGS. 18(a) to (c) are views illustrating the detection procedure by the detection device 106 of the substance to be measured according to the sixth embodiment of the present disclosure. The detection procedure of the detection device 106 of the substance to be measured according to the sixth embodiment of the present disclosure will be described with reference to FIGS. 17 and 18 (a) to (c). Although FIGS. 17 and 18(a) to (c) show an example where the container 3 and the imaging device 4 are fixed, and the magnetic field applying unit 2 is moved, the present embodiment is not limited to such an example. That is, the magnetic field applying unit 2 may be fixed, and the container 3 and the imaging device 4 may be moved, or the magnetic field applying unit 2, the container 3 and the imaging device 4 may be moved in opposite directions to each other.

First, as shown in FIGS. 17 and 18(a), the magnetic field applying unit 2 is moved to the first position P1 where the first plane member (20a-1s) of the magnet 20a faces to the upper surface 31a of the solution 31. Movement of the magnetic field applying unit 2 is realized by the control of the control unit 43. At this time, by the magnetic field of the magnet 20a, the unreacted magnetic labeling substance 53, and the composite particles 54 which is the substance to be measured 51 combined with the magnetic labeling substance 53 are attracted to the upper surface 31a of the solution 31. On the other hand, since the other substance 52 is not attracted by the magnetic field of the magnet 20a, it remains at the bottom of the container 3.

Next, as shown in FIGS. 17 and 18(b), the magnetic field applying unit 2 is moved relative to the container 3 to the second position P2 vertically upward as shown by a direction of an arrow G. At this time, since the magnetic field applying unit is not moved laterally as in the case of the fifth embodiment, the unreacted magnetic labeled substance 53 and the composite particles 54 do not move laterally. Thus, the unreacted magnetic label 53 and composite particles 54 are only sedimented by gravity.

In the sixth embodiment, whether the sedimentation rate of any of the unreacted magnetic labeling substance 53 and the composite particles 54 is fast is determined based on the weight and size of the respective particles, the viscosity of the biological sample solution and the like, and is considered to be unexpectedly determined. In other words, it is considered that in some cases, the unreacted magnetic labeling substance 53 has a slower sedimentation rate than the composite particles 54, or in some cases, the unreacted magnetic labeling substance 53 has a faster sedimentation rate than the composite particles 54 due to the viscosity of the solution 31 or the like. In the case where the sedimentation rate of the unreacted magnetic labeling substance 53 is slower than that of the composite particles 54, when the magnetic field applying unit 2 is moved from the first position P1 through the second position P2 to the third position P3, the unreacted magnetic labeling substance 53 and the composite particles 54 become as follows. That is, more of the unreacted magnetic labeling substance 53 exists in the upper region than the region where more of the composite particles 54 are present. That is, in the region near the upper surface 31a of the solution 31, more of the unreacted magnetic labeling substance 53 is present, and more of the composite particles 54 is present in the region on the bottom side. At this time, the imaging unit 41 can efficiently capture an image of the composite particles 54 by imaging so as to focus on the region of the bottom side.

On the other hand, contrary to the above, in the case where the sedimentation rate of the unreacted magnetic labeling substance 53 is faster than the sedimentation rate of the composite particles 54, when the magnetic field applying unit 2 is moved from the first position P1 through the second position P2 to the third position P3, the unreacted magnetic labeling substance 53 and the composite particles 54 become as follows. That is, more of the unreacted magnetic labeling substance 53 is present in the region below the region where more of the composite particles 54 are present. That is, more of the composite particles 54 is present in the region near the upper surface 31a of the solution 31, and more of the unreacted magnetic labeling substance 53 is present in the region closer to the bottom side than the above region. At this time, the imaging unit 41 can capture an image of the composite particles 54 efficiently by focusing on the region near the upper surface 31a of the solution 31.

Although FIG. 17 shows an example of setting the first imaging area R1 in the vicinity of the upper surface 31a of the solution 31, the present embodiment is not limited to such an example, and it is possible to set the first imaging region R1 in a region lower than the vicinity of the upper surface 31a of the solution 31.

Next, as shown in FIG. 17, the magnetic field applying unit 2 is moved to the third position P3 so as not to prevent imaging of the upper surface 31a of the solution 31 by the imaging unit 41. That is, the magnetic field applying unit 2 is moved in a direction of an arrow H, so that the imaging unit 41 can capture an image of the material to be measured. Capturing an image by the imaging unit 41 is realized by the control of the control unit 43. At this time, for example, in the case where the sedimentation rate of the magnetic labeling substance 53 is slower than that of the composite particles 54, the composite particles 54 continue sedimentation at a faster rate than the magnetic labeling substance 53, so that more of the composite particles 54 is present in the region in the downward direction lower than the region where more of the magnetic labeling substance 53 is present. That is, as shown in FIGS. 17 and 18 (c), only the unreacted magnetic labeling substance 53 is present in the first imaging area R1 vicinity the upper surface 31a of the solution 31, and only the composite particles 54 is present in the second imaging region R2 closer to the bottom side than the first imaging region R1. At this time, the imaging unit 41 can efficiently capture an image of the composite particles 54 by imaging so as to focus on the second imaging region R2. Thus, the magnetic field applying unit 2 can relatively move with respect to the container 3 between a first position P1 where the first plane member (20a-1s) of the magnet 20a which is a closest portion of the upper surface side of the solution 31 in the magnetic field applying unit 2 faces to the upper surface 31a of the solution 31, and a third position P3 where the magnetic field applying unit 2 does not interfere capturing an image of the upper surface 31a of the solution 31 by the imaging unit 41.

At this time, preferably, the magnetic field applying unit 2 move to the third position P3, after moving relative to the container 3 to the second position P2 where effect by the magnetic field does not affect the composite particles 54 in vertical direction upward from the first position P1. This is because, in the case where the magnetic field applying unit 2 is only slightly moved vertically upward from the first position P1, the magnetic field affects the composite particles 54, and when moving the magnetic field applying unit 2 in such a state in the horizontal direction, the composite particles 54 will also move in the horizontal direction under the influence of the magnetic field and move outside of the imaging range of the imaging unit 41. When moving the magnetic field applying unit 2 vertically upward relative to the container 3 from the first position P1 to the second position P2 where the influence of the magnetic field does not affect the composite particles 54 and moving to the third position P3, since the composite particles 54 settle downward in the vertical direction by gravity, it is possible to maintain a state of accommodating the composite particles 54 in the imaging range of the imaging unit 41 and to reliably observe the composite particles 54.

When the magnetic field applying unit 2 is moved away from the solution 31, the magnetic field applied to the solution 31 is released, and the composite particles 54 and the unreacted magnetic labeling substance 53 begin to settle by gravity. At this time, since the composite particles 54 are more affected by gravity as compared with the unreacted magnetic labeling substance 53, when the rate of sedimentation of the composite particles 54 is faster than the rate of sedimentation of the unreacted magnetic labeling substance 53 as shown in FIG. 18 (c), the particles present in the solution 31 will be different by the depth thereof. When focusing on the first imaging region R1, the unreacted magnetic labeling substance 53 can be recognized as a clear particle as in FIG. 19. On the other hand, since the composite particles 54 settle over time, it is possible to confirm the appearance of a blurred image. Further, when focusing on the second imaging region R2, it becomes possible to recognize the composite particles 54 as clear particles as in FIG. 20. In addition, the unreacted magnetic labeling substance 53 sedimented from the upper surface 31a of the solution 31 has passed through the second imaging area R2 and becomes recognizable as clear particles, and those deviated from the focal position of the second imaging region R2 becomes possible to confirm the appearance of a blurred image.

Figure 19:
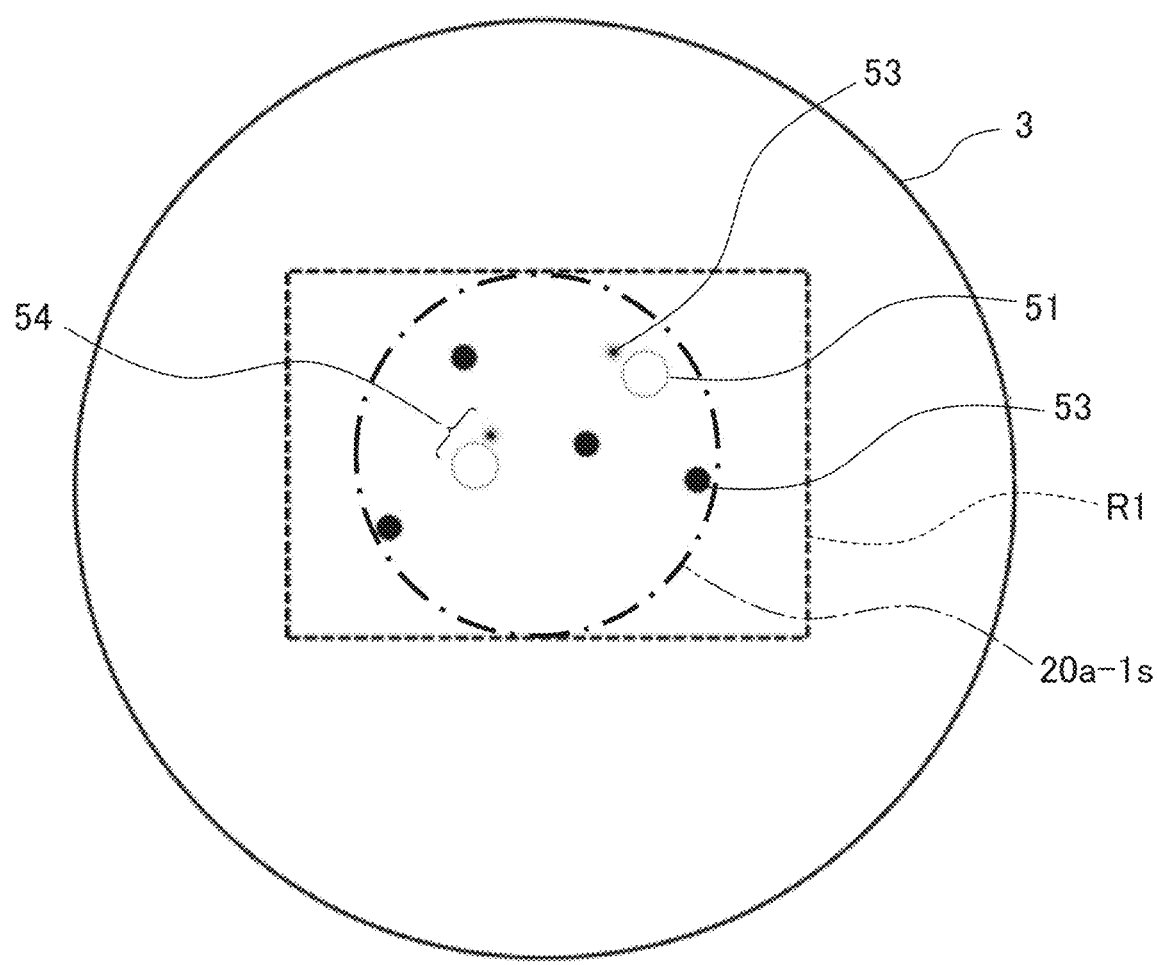
FIG. 19 is a diagram showing an example of an image of a first imaging region imaged by the detection device of the substance to be measured according to the sixth embodiment of the present disclosure.
Figure 20:
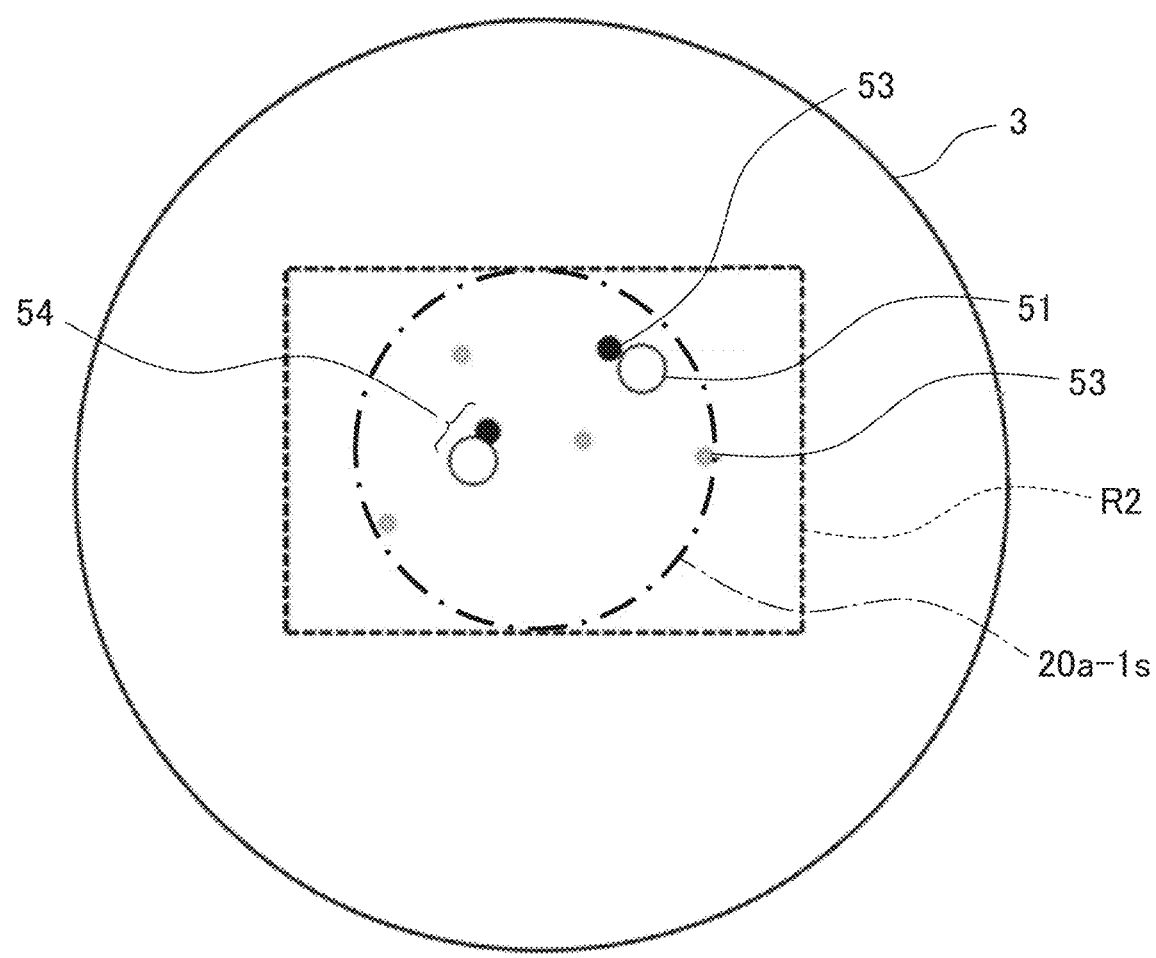
FIG. 20 is a diagram showing an example of an image of a second imaging region imaged by the detection device of the substance to be measured according to the sixth embodiment of the present disclosure.

Further, the magnetic field applying unit 2 applies a magnetic field to the solution 31, so that the composite particles 54 are distributed in the first imaging area R1 and the second imaging region R2 to be imaged by the imaging unit 41 (hereinafter, simply referred to as "imaging region (R1, R2)"). FIGS. 19 and 20 shows the positional relationship between the imaging region (R1, R2) and the first plane member (20a-1s) which is the bottom surface portion of the magnet 20a constituting the magnetic field applying unit 2. Since the region of the first plane member (20a-1s) which is the bottom surface portion of the magnet 20a has a shape to fit in the imaging region (R1, R2), a strong magnetic field is applied in the imaging region (R1, R2) and the composite particles 54 can be collected in the imaging region (R1, R2).

Preferably, the imaging area (R1, R2) imaged by the imaging unit 41 is a part of the region occupied by the container 3, and the first plane member (20a-1s) which is a closest portion of the upper surface side of the solution 31 in the magnet 20a which is a magnetic field applying unit has the size included in the imaging region (R1, R2). Thus, since the imaging area (R1, R2) imaged by the imaging unit 41 is smaller than the area occupied by the container 3, it is possible to increase the resolution of the image captured by the imaging unit 41. Further, as described above, since the size of the first plane member (20a-1s) which is the bottom surface portion of the magnet 20a has the size included in the imaging area (R1, R2), it is possible to collect the composite particles 54 included in the imaging region (R1, R2). As a result, it becomes possible to efficiently observe the composite particles 54 present in the solution 31.

A magnet used as a magnetic field applying unit in the detection device of the substance to be measured according to the sixth embodiment will be described. FIGS. 21(a) to (h) shows an example of a magnet used as a magnetic field applying unit in the detection device of the substance to be measured according to the sixth embodiment of the present disclosure. FIG. 21(a) is a perspective view of a magnet 20a laminated by three cylindrical magnets (20a-1, 20a-2, 20a-3) with different diameters each other. It is assumed that the solution containing the composite particles in which a magnetic labeling substance is bonded to the substance to be measured is disposed below the magnet 20a in a vertical direction, and an imaging unit is disposed above the magnet 20a in a vertical direction. At this time, the magnet is arranged so that an area of the first plane member (20a-1s) viewed from the solution side of the magnet (20a-1) disposed on the solution side is smallest and an area of the second plane member (20a-3s) viewed from the solution side of the third magnet (20a-3) disposed on the imaging portion side is largest. That is, assuming that the plane of the second stage magnet (20a-2) viewed from the solution side is (20a-2s), the following relationship is established.

Area of (20a-1s)<Area of (20a-2s)<Area of (20a-3s)

Therefore, the magnet 20a has the first plane member (20a-1s) facing the upper surface of the solution and the second plane member (20a-3s) facing the imaging unit, and the area of the first plane member (20a-1s) is smaller than the area of the second plane member (20a-3s). Further, by setting the range occupied by the first plane member (20a-1s) within the imaging region of the imaging unit, the composite particles can be collected in the first plane member (20a-1s), and it is possible to detect the composite particles efficiently.

Furthermore, by laminating a magnet having a larger cross-sectional area than the first plane member, a larger magnetic field can be generated than when using a cylinder having a constant cross-sectional area which is the same as the area of the first plane member, it is possible to attract the composite particles efficiently.

FIG. 21(b) is a perspective view of a magnet 20b laminated by two cylindrical magnets (20b-1, 20b-2) having different diameters. It is assumed that the solution containing the composite particles in which the magnetic labeling substance is bonded to the substance to be measured is disposed below the magnet 20b in the vertical direction, and an imaging unit is disposed above the magnet 20b in the vertical direction. At this time, the magnet is arranged so that the area of the first plane member (20b-1s) viewed from the solution side of the magnet (20b-1) disposed on the solution side is smaller than the area of the second plane member (20b-2s) viewed from the solution side of the magnet (20b-2) disposed on the imaging portion side. That is, the following relationship holds.

Area of (20b-1s)<Area of (20b-2s).

Therefore, the magnet 20b has a first plane member (20b-1s) opposed to the upper surface of the solution and a second plane member (20b-2s) opposed to the imaging unit, and the area of the first plane member (20b-1s) is smaller than the area of the second plane member (20b-2s). Further, by setting the range occupied by the first plane member (20b-1s) within the imaging region of the imaging unit, the composite particles can be collected within the first plane member (20b-1s), and it is possible to detect the composite particles efficiently.

FIG. 21(c) shows an example of a configuration of a conical magnet 20c having a flat portion at the distal end. It is assumed that the solution containing the composite particles in which the magnetic labeling substance is bonded to the substance to be measured is disposed below the magnet 20c in the vertical direction, and an imaging unit is disposed above the magnet 20c in a vertical direction. At this time, the magnet 20c, which is the magnetic field applying unit, has a shape in which the cross-sectional area increases continuously or stepwise as it advances upward from the lower end of the magnet 20c. That is, the magnet has a first plane member (20c-s1) facing the upper surface of the solution, and has a configuration so that the cross-sectional area of a cross-section (20c-s (d)) parallel to the first plane member (20c-s1) at a position vertically upward from the first plane member (20c-s1) by a predetermined distance is larger than the area of the first plane member (20c-s1). This is equivalent to laminating a plurality of magnets having a cross-sectional area larger than that of the first plane member (20c-s1). Therefore, the magnet 20c of the conical structure can generate a larger magnetic field than when using a cylinder having a constant cross-sectional area which is the same as the area of the first plane member (20c-s1), and can attract the composite particles efficiently.

FIG. 21(d) is a perspective view of a magnet 20d in which three prismatic magnets (20d-1, 20d-2, 20d-3) having different cross-sectional areas perpendicular to the axial direction are laminated. It is assumed that the solution containing the composite particles in which the magnetic labeling substance is bonded to the substance to be measured is disposed below the magnet 20d in a vertical direction, and an imaging unit is disposed above the magnet 20d in a vertical direction. At this time, the magnet is arranged so that an area of the first plane member (20d-1s) viewed from the solution side of the magnet (20d-1) disposed on the solution side is smallest and an area of the second plane member (20d-3s) viewed from the solution side of the magnet (20d-3) disposed on the imaging portion side is largest. That is, assuming that the plane of the second stage magnet (20d-2) viewed from the solution side is (20d-2s), the following relationship is established.

Area of (20d-1s)<Area of (20d-2s)<Area of (20d-3s)

Therefore, the magnet 20d has a first plane member (20d-1s) facing the upper surface of the solution, and a second plane member (20d-3s) facing the imaging unit, and the area of the first plane member (20d-1s) is smaller than the area of the second plane member (20d-3s). Further, by setting the range occupied by the first plane member (20d-1s) within the imaging region of the imaging unit, the composite particles can be collected within the first plane member (20d-1s), and it is possible to detect the composite particles efficiently. Furthermore, by laminating a magnet having a larger cross-sectional area than the first plane member, a larger magnetic field can be generated than when using a prism having a constant cross-sectional area which is the same as in the area of the first plane member, it is possible to attract the composite particles efficiently.

FIG. 21(e) is a perspective view of a magnet 20e in which two prismatic magnets (20e-1, 20e-2) having different cross sectional areas perpendicular to the axial direction are laminated. It is assumed that the solution containing composite particles in which a magnetic labeling substance is bonded to the substance to be measured is disposed below the magnet 20e in a vertical direction, and an imaging unit is disposed above the magnet 20e in a vertical direction. At this time, the magnet is arranged so that an area of the first plane member (20e-1s) viewed from the solution side of the magnet (20e-1) disposed on the solution side is smaller than an area of the second plane member (20e-2s) viewed from the solution side of the magnet (20e-2) disposed on the imaging portion side. That is, the following relationship holds. Area of (20e-1s)<Area of (20e-2s)

Therefore, the magnet 20e has a first plane member (20e-1s) facing the upper surface of the solution, and a second plane member (20e-2s) facing the imaging unit, and the area of the first plane member (20e-1s) is smaller than the area of the second plane member (20e-2s). Further, by setting the range occupied by the first plane member (20e-1s) within the imaging region of the imaging unit, the composite particles can be collected within the first plane member (20e-1s), and it is possible to detect the composite particles efficiently.

Figure 21:
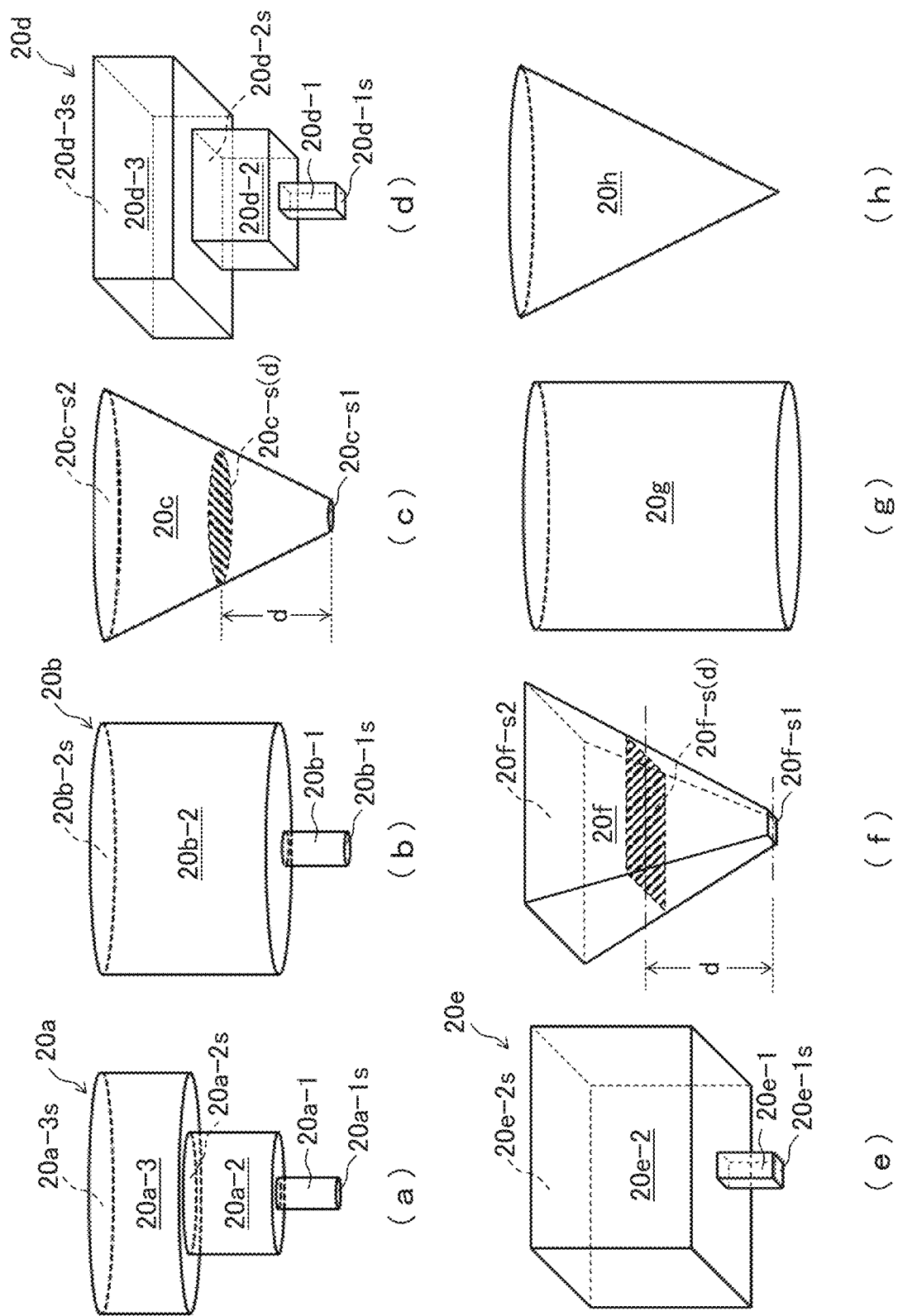
FIGS. 21(a) to 21(h) are diagrams showing examples of magnets used as a magnetic field applying unit in the detection device of the substance to be measured according to the sixth embodiment of the present disclosure.

In FIGS. 21 (a), (b), (d), and (e), as an example of laminating a plurality of magnets, examples of laminating two or three magnets having a cylindrical shape or a prismatic shape with different diameter are shown. However, the present embodiment is not limited to such an example and four or more magnets may be laminated. Further, although the above examples shows examples in which a plurality of magnets are overlapped with each other, a plurality of magnets to be laminated may be integrally molded.

FIG. 21(f) shows an example of a configuration of a pyramid-shaped magnet 20f having a flat portion at the distal end. It is assumed that the solution containing composite particles in which a magnetic labeling substance is bonded to the substance to be measured is disposed below the magnet 20f in a vertical direction, and an imaging unit is disposed above the magnet 20f in a vertical direction. At this time, the magnet has a first plane member (20f-s1) facing the upper surface of the solution, and the magnet has a configuration in which the cross-sectional area of the cross section (20f-s (d)) parallel to the first plane member (20f-s1) increases as it proceeds vertically upward from the first plane member (20f-s1). This is equivalent to laminating a plurality of magnets having a cross-sectional area larger than that of the first plane member (20f-s1). Therefore, the magnet 20f of the pyramidal structure can generate a larger magnetic field than when using a prism having a constant cross-sectional area which is the same as the area of the first plane member (20f-s1), and can attract the composite particles efficiently.

A cylindrical magnet 20g shown in FIG. 21(g) is composed of a single cylinder and has a structure in which the areas of both ends are equal. A conical magnet 20h shown in FIG. 21(h) is a simple cone and does not have a planar portion of a predetermined size at the distal end. Magnets 20g and 20h are exemplified for comparison with the configuration in which a plurality of cylindrical magnets are laminated, as described later.

Figure 22:
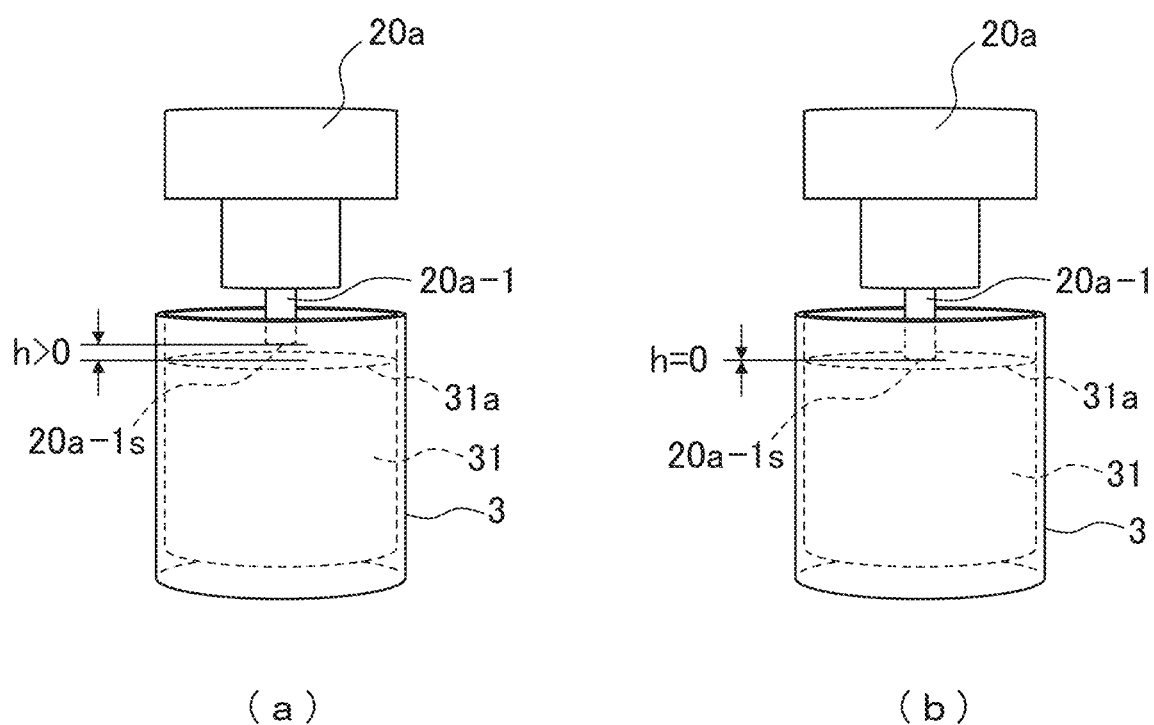
FIGS. 22(a) and 22(b) are perspective views showing the positional relationship when brought into contact with the case where the magnet and the solution held in the holder in the detection device of the substance to be measured according to the sixth embodiment of the present disclosure is spaced apart, FIG. 22 (a) shows the positional relationship when the magnet and the solution held in the holder are spaced apart, and FIG. 22 (b) shows the positional relationship when both of them are brought into contact with each other.

In the detection device of the substance to be measured according to the sixth embodiment of the present disclosure, the positional relationship when the magnet held in the holder and the solution are separated from each other is shown in FIG. 22(a), and the positional relationship when both of them are brought into contact with each other is shown in FIG. 22(b). It is assumed that a distance between the first plane member (20a-1s) of the solution 31 side of the first stage magnet (20a-1) of the solution 31 side and the upper surface 31a of the solution 31 in the magnet 20a in which three cylindrical magnets are laminated is h. In FIG. 22(b), "h=0" indicates that the distance from the magnet 20a to the upper surface 31a of the solution 31 is zero. In FIGS. 22(a) and (b), the magnet 20a is held by the holder and the distance between the magnet 20a and the solution 31 is determined, but the description of the holder is omitted for the sake of simplicity.

Figure 23:
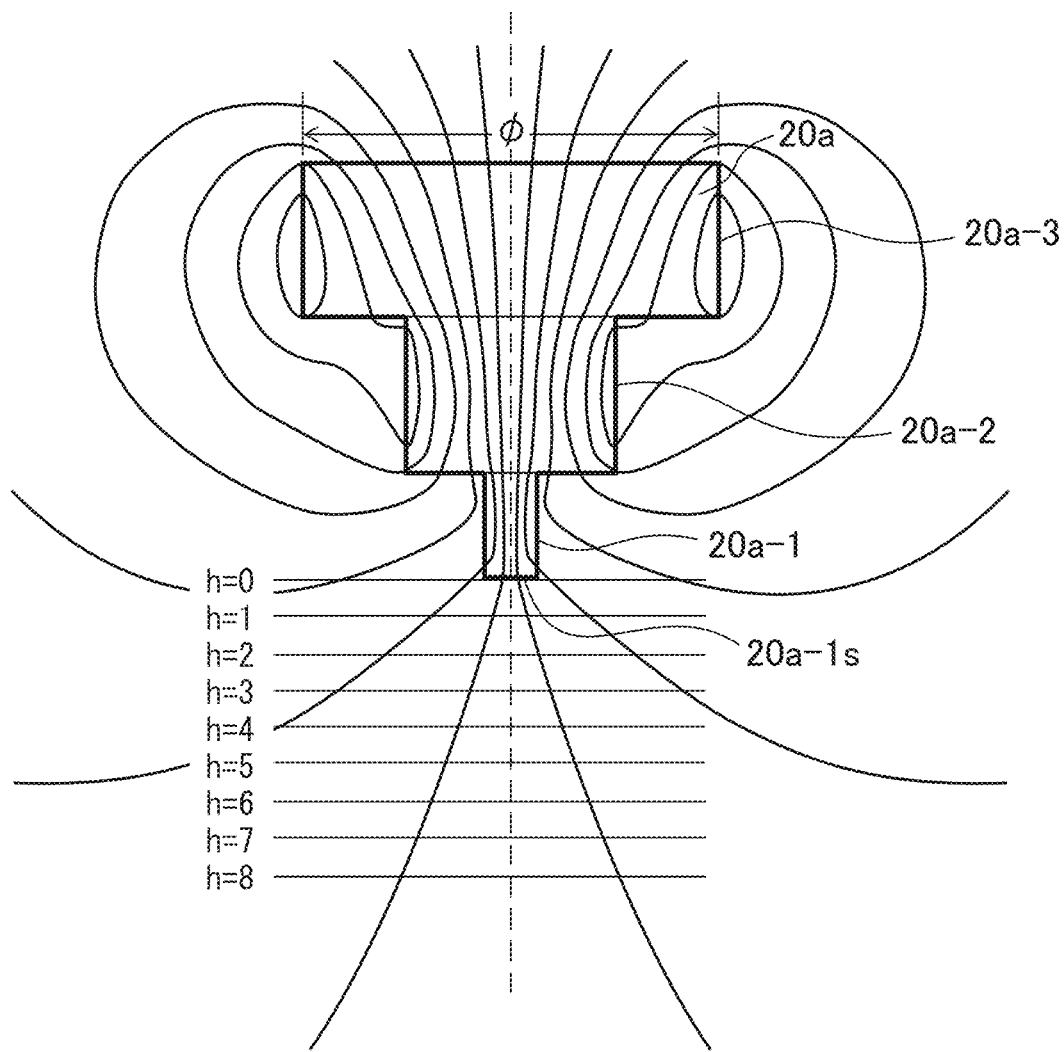
FIG. 23 is a diagram showing a magnetic flux generated when three cylindrical magnets having different diameters are connected, which are used in the detection device of the substance to be measured according to the sixth embodiment of the present disclosure.

FIG. 23 shows a magnetic flux diagram generated in the magnet 20a (see FIG. 21 (a)) having three cylindrical magnets (20a-1, 20a-2, 20a-3) with different diameters connected with each other, which is used in the detection device of the substance to be measured according to the sixth embodiment of the present disclosure. The maximum value of the diameter<p of the magnet 20a shown in FIG. 23 is 8 [mm], and the diameter at the tip portion below in the vertical direction is 1 [mm]. A neodymium magnet is used for the magnet 20a. The term "h" is the distance from the first plane member (20a-1s) of the magnet 20a, and the unit is [mm]. In FIG. 23, a dotted line extending in the vertical direction from the vicinity of the center of the magnet 20a indicates the position of the center of the magnet 20a.

Figure 24:
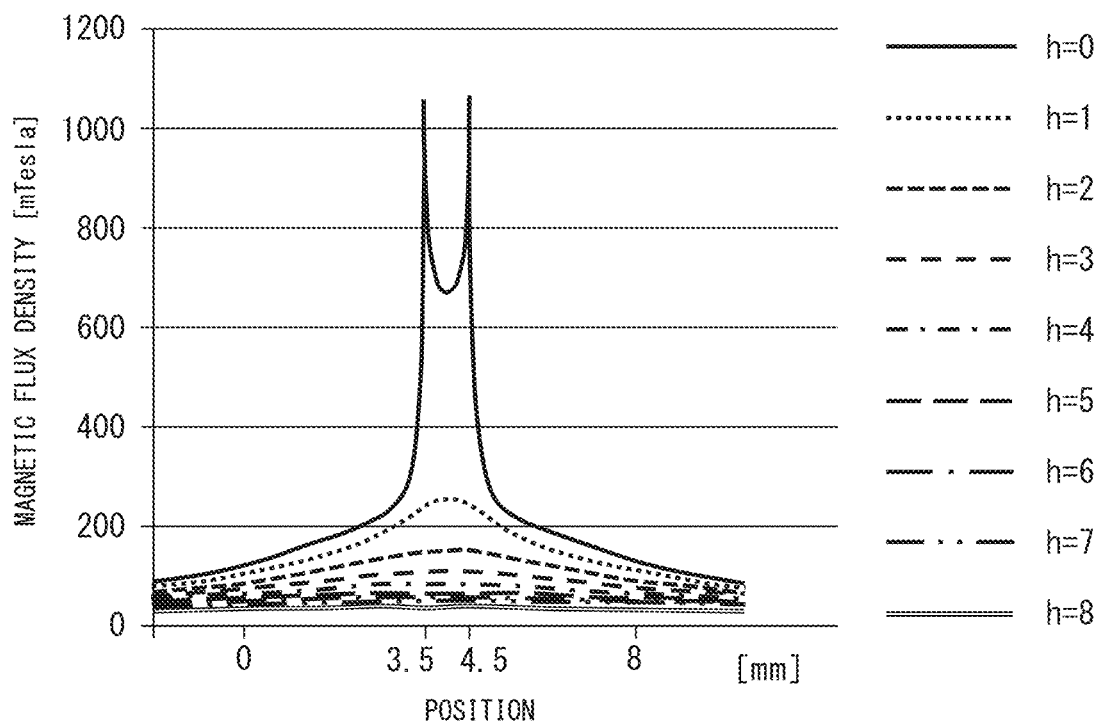
FIG. 24 is a graph showing the magnitude of the magnetic flux density in the horizontal direction when changing the distance from the bottom surface of the magnet in FIG. 23.

FIG. 24 shows a graph showing the magnitude of the magnetic flux density in the horizontal direction when the distance from the first plane member (20a-1s) of the magnet 20a is changed in FIG. 23. Horizontal axis indicates the position of the third stage magnet (20a-3) from the end portion at which the diameter of the magnet 20a is the largest, and the vertical axis is the magnetic flux density [mTesla]. If h=0 where the magnet 20a and the solution 31 are in contact with each other, corresponding to the shape of the first stage magnet (20a-1) which is the tip of the magnet 20a, the magnetic flux density at the position of 3.5 [mm] and 4.5 [mm] shows a maximum value. On the other hand, when the distance h between the magnet 20a and the solution 31 is 1 [mm], the effect of the shape of the first stage magnet (20a-1), which is a tip portion of the magnet 20a, is less than in the case of h=0, the magnetic flux density is maintained to some extent while drawing a relatively smooth curve. On the other hand, when the distance h is 2 [mm] or more, it can be seen that the magnetic flux density decreases sharply and the magnetic force for attracting the composite particles and the unreacted magnetic labeling substance becomes weak. Therefore, from the graph of FIG. 24, it can be said that it is preferable that the distance h between the magnet 20a and the solution 31 is about 1 [mm].

Figure 25:
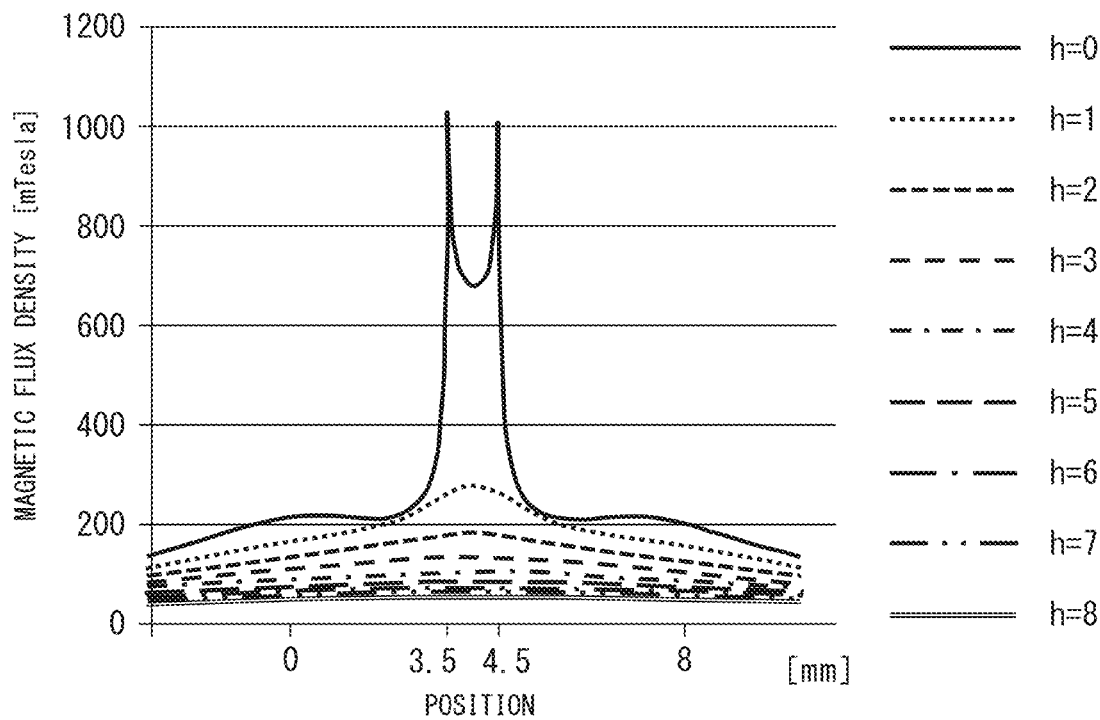
FIG. 25 is a graph showing the magnitude of the magnetic flux density in the horizontal direction when changing the distance from the bottom surface of the magnet in the magnetic field generated when connecting the two cylindrical magnets having different diameters.

FIG. 25 shows a graph showing the magnitude of the magnetic flux density in the horizontal direction when the distance from the first plane member (20b-1s) which is the bottom surface of the magnet (20b-1) is changed in the magnetic field generated when the two cylindrical magnets (20b-1, 20b-2) having different diameters shown in FIG. 21(b) are connected. In the magnet 20b, since the shape of the magnet (20b-1) on the solution side is similar to that of the magnet (20a-1) on the solution side of the magnet 20a, the intensity of the magnetic flux density is similar to that in FIG. 24. However, in the case of the magnet 20b, since two cylindrical magnets (20b-1, 20b-2) are laminated and the magnet (20b-2) on the imaging unit side is also close to the solution, the curve is raised at a position away from the center than in the case of FIG. 24. This means that a strong magnetic field is also generated around the magnet (20b-1) on the solution side, and the composite particles and the unreacted magnetic labeling substance may also be attracted to the periphery of the magnet (20b-1). Therefore, in order to achieve the purpose of collecting the composite particles and the unreacted magnetic labeling substance in a narrow range on the solution side, it is considered preferable to constitute so that the diameter of the magnet on the solution side becomes small as in the magnet 20a rather than the magnet 20b.

Figure 26:
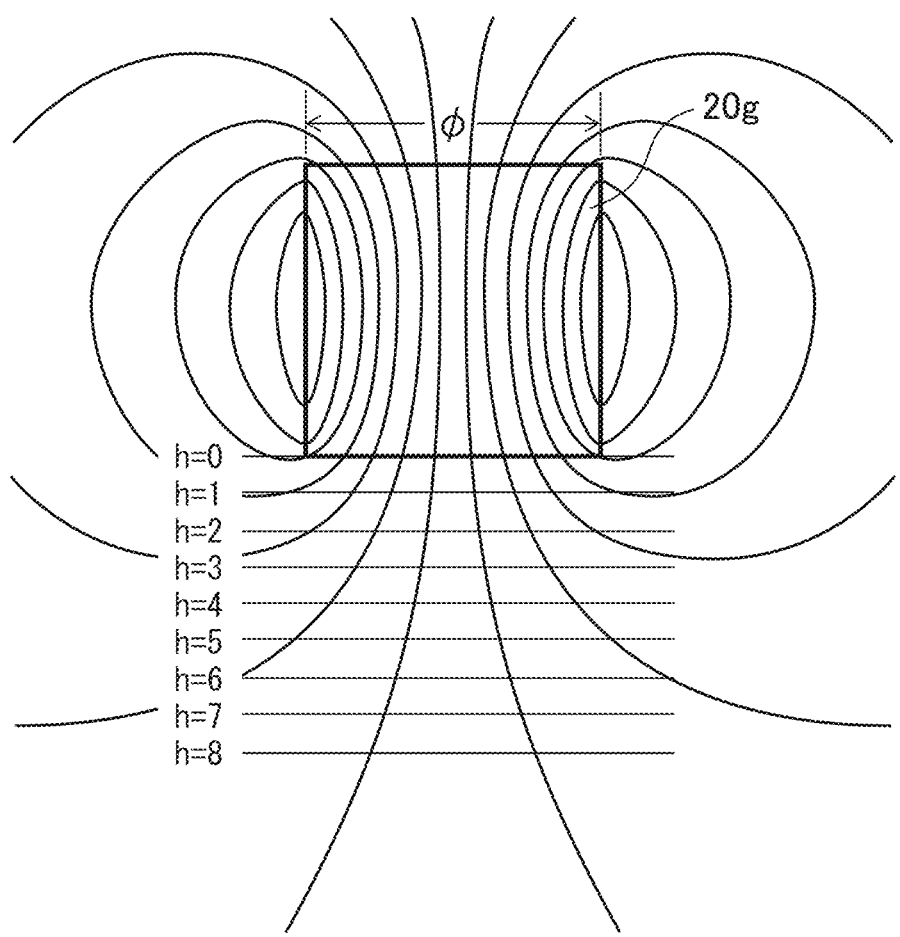
FIG. 26 is a diagram showing a magnetic flux diagram resulting from the cylindrical magnet.

FIG. 26 shows a magnetic flux diagram resulting from the cylindrical magnet 20g shown in FIG. 21 (g). The diameter φ is 8 [mm].

Figure 27:
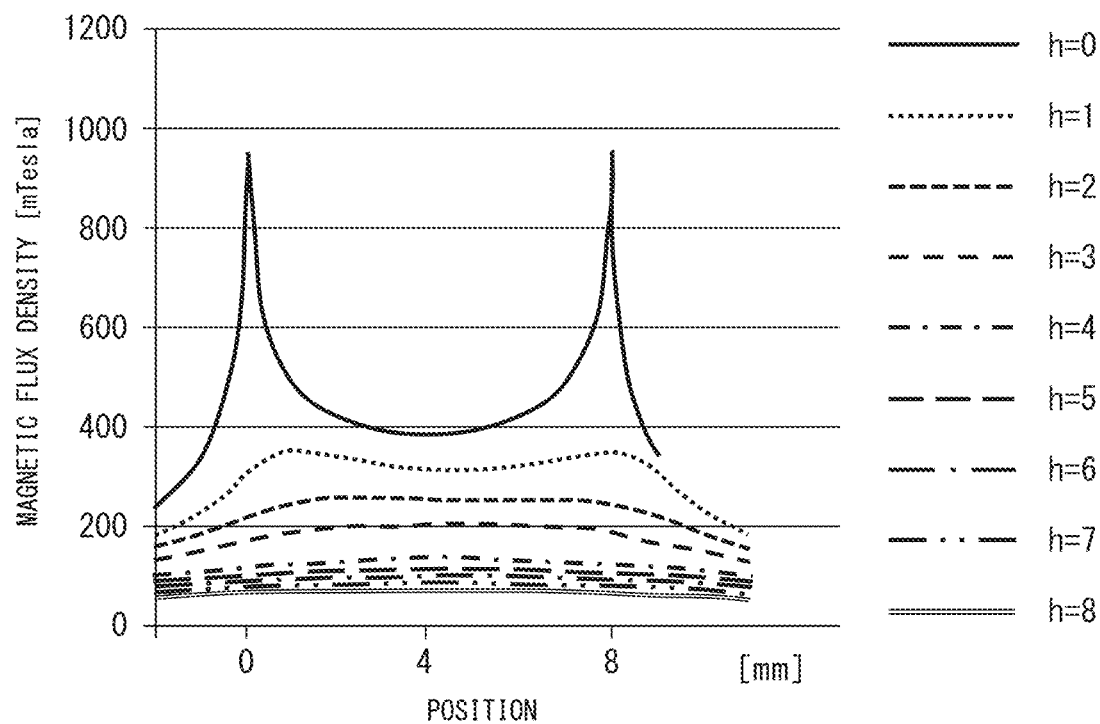
FIG. 27 is a graph showing the magnitude of the magnetic flux density in the horizontal direction when changing the distance from the bottom surface of the magnet in the magnetic field resulting from the cylindrical magnet.

FIG. 27 shows a graph showing the magnitude of the magnetic flux density in the horizontal direction when the distance from the bottom surface of the magnet is changed in FIG. 26. The horizontal axis indicates the position from the end of the part where the diameter of the magnet 20g is the largest, and the vertical axis is the magnetic flux density [mTesla]. When h=0 where the magnet 20g and the solution are in contact with each other, the magnetic flux density shows a maximum value at the position of 0 [mm] and 8 [mm] corresponding to both ends of the magnet 20g. Furthermore, even though when the distance h between the magnet 20g and the solution is 1 [mm], the maximum value corresponding to the shape of both ends of the magnet 20g decreases sharply compared to the case of h=0, it can be seen that the magnetic field at both ends is still stronger than the central portion. Further, when the distance h is 2 [mm], while the magnetic flux density can be made uniform over a wide range of about 2 to 6 [mm], it is considered difficult to generate a strong magnetic field near the center. Therefore, when the horizontal distance of the observation area is 2 [mm] or less, the composite particles collected by the magnet 20g are also distributed outside the observation area, and when collecting the composite particles in the observation area, it is considered preferable to use the magnet 20a rather than 20g.

Figure 28:
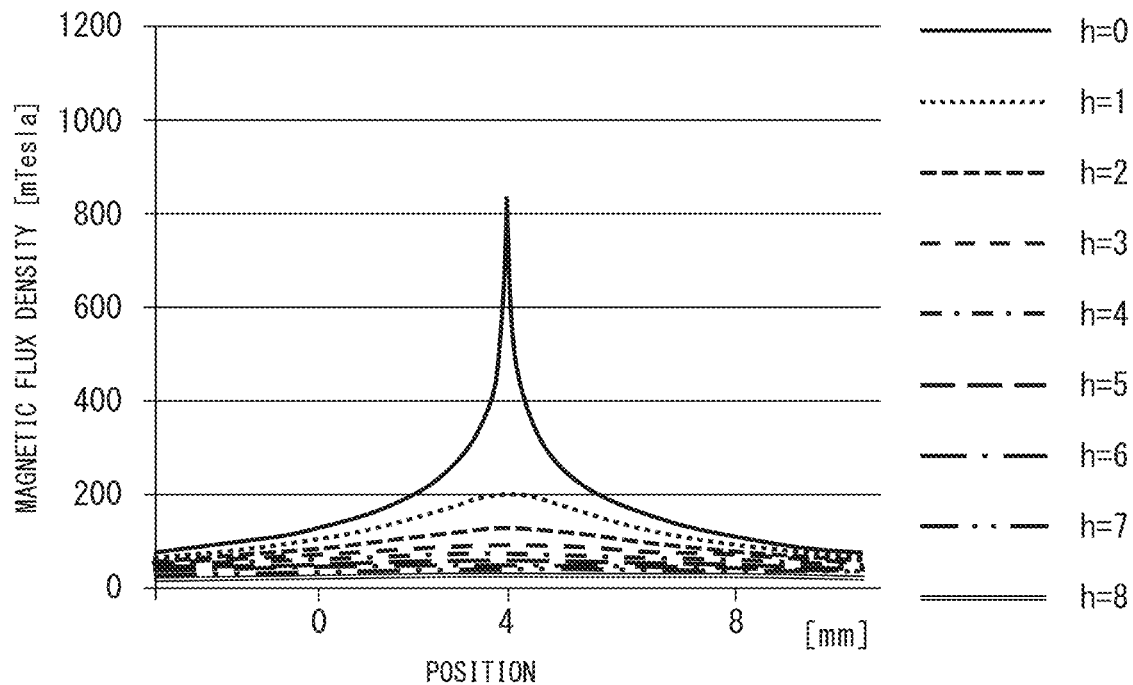
FIG. 28 is a graph showing the magnitude of the magnetic flux density in the horizontal direction when changing the distance from the tip of the magnet in the magnetic field resulting from the conical magnet.

FIG. 28 shows a graph indicating the magnitude of the magnetic flux density in the horizontal direction when the distance from the tip of the magnet is changed in the magnetic field resulting from the conical magnet 20h shown in FIG. 21(h). The horizontal axis indicates the position from the end of the part where the diameter of the magnet 20h is the largest, and the vertical axis is the magnetic flux density [mTesla]. When h=0 where the magnet 20h and the solution are in contact with each other, the magnetic flux density shows the maximum value at the position of 4 [mm] corresponding to the central portion of the magnet 20h. Further, when the distance h between the magnet 20h and the solution is 1 [mm], the maximum value of the magnetic field at the center of the magnet 20h is reduced compared to when h=0. Therefore, it is necessary to bring the tip of the magnet 20h close to the solution in order to obtain a strong magnetic field. However, if they are too close to each other, the magnetic field is maximized only in the center part, and the composite particles are concentrated in one place, which makes it difficult to measure the number of composite particles. Therefore, it is considered preferable that the shape of the portion of the magnet facing the solution is a flat surface having a certain area.

Further, the magnets 20a to 20f (FIGS. 21(a) to (f)) can have a larger volume to fill a predetermined rectangular parallelepiped space than the magnet 20h (FIG. 21(h)). Therefore, when a predetermined rectangular parallelepiped space is given as a space for arranging the magnets, the magnets 20a to 20f can have a larger filling rate of the space than the magnet 20h, so that the magnetic field can be increased.

Figure 29:
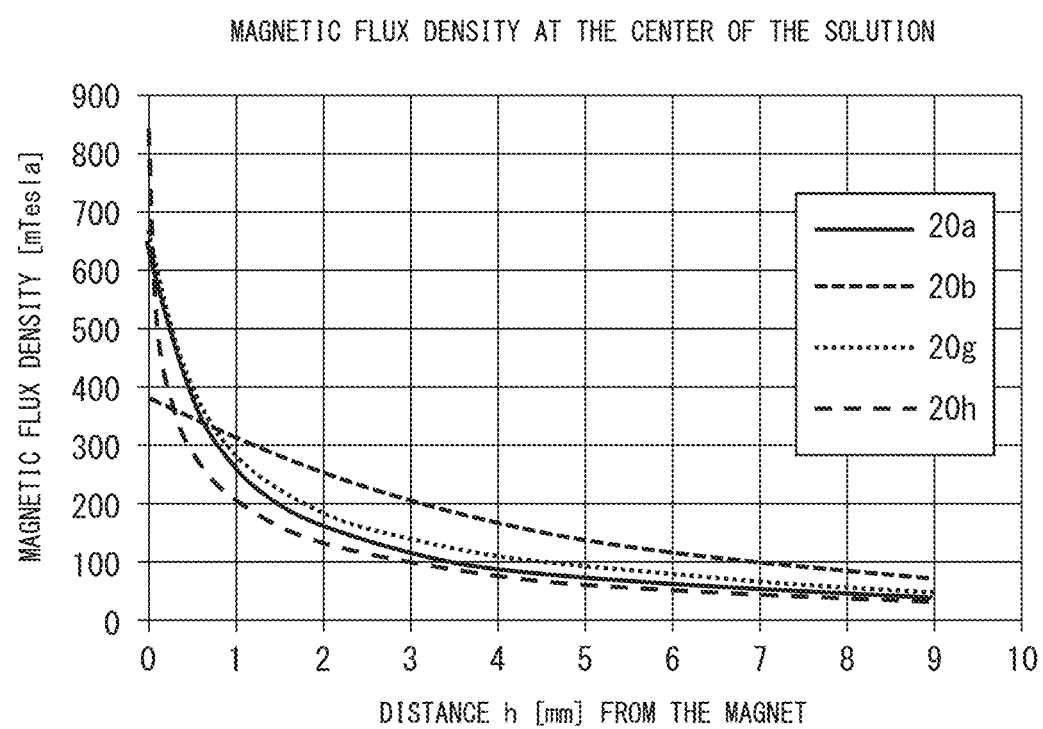
FIG. 29 is a graph showing the relationship between the distance and the magnetic flux density from the center of the magnet in various magnets with different shape.

FIG. 29 shows a graph showing the relationship between the distance from the center portion of the magnet and the magnetic flux density in various magnets having different shapes. The horizontal axis is the distance h[mm] from the tip of the solution-side at the center of the magnet, and the vertical axis is the magnetic flux density [mTesla]. The magnets used in the calculation are the magnet 20a with three cylinders connected, the magnet 20b with two cylinders connected, a single cylindrical magnet 20g, and a conical magnet 20h as shown in FIGS. 21(a), (b), (g), and (h), respectively. FIG. 29 shows that the magnetic flux density at the center of upper surface of the solution becomes stronger as the distance between the solution and the magnet is closer to zero, and the distribution reflects the shape of the opposing magnets. From this, it can be seen that it is advantageous to make the shape of the magnet tapered in order to attract the composite particles and the unreacted magnetic labeling substance.

FIG. 30 shows an example of a holder for holding a magnet used in the detection device of the substance to be measured according to the sixth embodiment of the present disclosure. FIGS. 20(a) to (c) are plan view, a side view, and a perspective view of the holder 90, respectively. An opening 91 for mounting a magnet (not shown) is provided near the end of the holder 90, and a holding portion 92 for holding the magnet is provided on the bottom side of the holder 90.

FIGS. 31(a) and (b) show the positional relationship between the magnet held in the holder and the solution in the detection device of the substance to be measured according to the sixth embodiment of the present disclosure. FIG. 31(a) shows an example in which the magnet 20a laminated with three cylindrical magnets is attached to the holder 90 shown in FIGS. 30(a) to (c). Among the three magnets constituting the magnet 20a, the second stage magnet (20a-2) is held by the holding portion 92. Further, when the first stage magnet (20a-1) protrudes from the holder 90 and the magnet 20a is brought close to the container 3, the first plane member (20a-1s) is opposed to and separated from the upper surface 31a of the solution 31 by a distance $h_1$. The entire of the first stage magnet (20a-1) protrudes from the holder 90 (located under the holder 90), so that the first plane member (20a-1s) of the first stage magnet (20a-1) is easily close to the upper surface 31a of the solution 31. Further, by arranging the holder 90 so that the lower surface of the holder 90 comes into contact with the upper end of the container 3 (the edge of the container 3) and predetermining the amount of the solution 31 to be placed in the container 3, the following advantages are obtained. That is, it is possible to suppress the distance $h_1$ between the first plane member (20a-1s) and the upper surface 31a of the solution 31 varies from measurement to measurement. Further, by adjusting the width of the holding portion 92 to the width of the container 3, since the holding portion 92 fits into the container 3, so that the position of the first stage magnet (20a-1) in the direction parallel to the upper surface 31a, it is possible to suppress the variation from measurement to measurement. Further, the third stage magnet (20a-3) is exposed on the upper side of the holder 90. By controlling the position of the holder 90, it is possible to control the positional relationship between the magnet 20a and the solution 31.

FIG. 31 (b) shows the structure of the other holder 90a. The holder 90a has a structure in which the holding portion 93 of the magnet is not provided with on the surface of the holder 90a, but is provided inside the holder 90a. The holding portion 93 provided inside the holder 90a holds the second stage of the magnet (20a-2). In the configuration of the holder 90 shown in FIG. 31(a), whereas the thickness of the holder 90 is the same as the thickness of the second stage magnet (20a-2), in the configuration of the holder 90a shown in FIG. 31(b), the thickness of the holder 90a is thicker than the second stage magnet (20a-2). Therefore, if the thickness of the first stage of the magnet (20a-1) is the same, the configuration of the holder 90 shown in FIG. 31(a) is easy to approach the first stage of the magnet (20a-1) to the upper surface 31a of the solution 31, as compared with the configuration of the holder 90a shown in FIG. 31(b). That is, when the shape of the container 3 and the amount of the solution 31 are the same in the holder 90 shown in FIG. 31(a) and the holder 90a shown in FIG. 31 (b), assuming that the distance between the first plane member (20a-1s) in the holder 90a shown in FIG. 31(b) and the upper surface 31a of the solution 31 as $h_2$, $h_1$ can be made smaller than $h_2$. Similarly, the configuration of the holder 90 shown in FIG. 31(a) makes it easier to bring the second stage of the magnet (20a-2) closer to the upper surface 31a of the solution 31 than the configuration of the holder 90a shown in FIG. 31(b). Other structures of the holder 90a are the same as the structure of the holder 90 shown in FIG. 31(a). By controlling the position of the holder 90a, it is possible to control the positional relationship between the magnet 20a and the solution 31.

In the description of the sixth embodiment, an example in which the imaging unit is disposed above the container is shown, but the present embodiment is not limited to such an example, and the imaging unit may be disposed below the container. That is, FIGS. 17 and 18(a) to (c) shows an example in which the imaging device 4 having the imaging unit 41, the detection unit 42, and the control unit 43 is arranged above the container 3, but the imaging device 4 may be arranged below the container 3 as in the imaging device 4a having the imaging unit 41a, the detection unit 42a, and a control unit 43a, shown in FIG. 7. With such a configuration, the imaging unit, it is possible to image the composite particles collected in the predetermined region without being blocked by the magnetic field applying unit.

In the above description, the case where another substance that is not an object to be measured is settled by to gravity in the solution has been described as an example. However, even when other substances move in the solution in the direction opposite to gravity, the detection device of the embodiments of the present disclosure can be utilized. In other words, the magnetic field applying unit may be provided in the lower part of the container so that the substance to be measured to which the magnetic labeling substance is bound in the direction opposite to that of the other substances. The position of the substance to be measured can be separated from the other substance in the solution by arranging the magnetic field applying unit at an appropriate position according to the behavior of the other substance in the solution.

According to the detection device of a substance to be measured according to the embodiments of the present disclosure described above, it is possible to detect bacteria, fungi and the like having a size of several microns in solution.

The invention claimed is:

1. A detection device comprising:
    a container that contains solution and a composite particle combining a substance to be measured and a magnetic labeling substance;
    a magnetic field applying unit that applies a magnetic field to a predetermined region so as to collect the composite particle, wherein spatial light is incident to the predetermined region other than lower region of the container;
    an imaging unit that captures an image of the composite particle collected in the predetermined region where the spatial light is incident; and
    a detecting unit that detects the composite particle based on the image captured by the imaging unit
    wherein the imaging unit is disposed at a position facing the container across the magnetic field applying unit, and
    wherein the magnetic field applying unit moves to a position relative to the container where the magnetic field applying unit does not interfere capturing the image by the imaging unit when the imaging unit captures the image.

2. The detection device according to claim 1, wherein the magnetic field applying unit includes:
    a first plane member opposed to the upper surface of the solution; and
    a second plane member facing the imaging unit, and
    wherein an area of the first plane member is smaller than an area of the second plane member.

3. The detection device according to claim 1, wherein the magnetic field applying unit has a shape in which the cross-sectional area increases continuously or stepwise, as it proceeds upward from the lower end of the magnetic field applying unit.

4. The detection device according to claim 1, wherein the magnetic field applying unit applies a magnetic field to the solution so that the composite particle is distributed in an imaging region where the imaging unit captures an image.

5. The detection device according to claim 1,
    wherein the imaging region captured by the imaging unit is a part of the region occupied by the container, and
    wherein the closest portion of the upper surface side of the solution in the magnetic field applying unit has a size included in the imaging region.

6. The detection device according to claim 2, wherein the magnetic field applying unit has a plurality of laminated magnets.

7. The detection device according to claim 2, wherein the magnetic field applying unit has an integrally molded magnet.

8. The detection device according to claim 6, wherein the plurality of magnets have a cylindrical shape or a prismatic shape.

9. The detection device according to claim 1, the magnetic field applying unit is relatively movable with respect to the container between a position where a closest portion of an upper surface side of the solution in the magnetic field applying unit opposed to the upper surface of the solution and a position where the magnetic field applying unit does not interfere with the imaging unit capturing an image of the upper surface of the solution.

10. The detection device according to claim 9, further comprising a control unit for controlling the magnetic field applying unit so that the magnetic field applying unit moves relative to the container to the position where the magnetic field applying unit does not interfere with capturing an image by the imaging unit, after the closest portion of the magnetic field applying unit moves vertically upward to a position where the influence of the magnetic field does not affect the composite particles from a position facing the upper surface of the solution.

11. A detection device comprising:

a container that contains solution and a composite particle combining a substance to be measured and a magnetic labeling substance;

a magnetic field applying unit that applies a magnetic field to a predetermined region so as to collect the composite particle, wherein spatial light is incident to the predetermined region other than lower region of the container;

an imaging unit that captures an image of the composite particle collected in the predetermined region where the spatial light is incident; and a detecting unit that detects the composite particle based on the image captured by the imaging unit wherein the magnetic field applying unit is disposed above the container, and wherein the imaging unit is disposed below the container.

12. A detection device comprising:

a container that contains solution and a composite particle combining a substance to be measured and a magnetic labeling substance;

a magnetic field applying unit that applies a magnetic field to a predetermined region so as to collect the composite particle, wherein spatial light is incident to the predetermined region other than lower region of the container;

an imaging unit that captures an image of the composite particle collected in the predetermined region where the spatial light is incident; and a detecting unit that detects the composite particle based on the image captured by the imaging unit wherein the magnetic field applying unit has a first coil, and wherein the imaging unit is disposed at a position facing the container across the first coil, so as to capture an image of the inside of the container through the inside of the first coil.

13. The detection device according to claim 12, wherein the magnetic field applying unit further includes a second coil, and wherein the second coil is disposed at a position such that a magnetic field can be applied to a position different from the position where the magnetic field is applied by the first coil.

14. The detection device according to claim 12, wherein the magnetic field applying unit further includes a second coil, and further comprising a control unit configuring to stop applying the magnetic field by the first coil after a first predetermined time has elapsed since start of the applying the magnetic field by the first coil, start applying the magnetic field by the second coil, and make the imaging unit capture an image after the second predetermined time has elapsed from the start of the applying the magnetic field by the second coil.

* * * * *